US010849550B2

(12) United States Patent
Branch et al.

(10) Patent No.: US 10,849,550 B2
(45) Date of Patent: Dec. 1, 2020

(54) ROBOTIC JOINT TESTING APPARATUS AND COORDINATE SYSTEMS FOR JOINT EVALUATION AND TESTING

(71) Applicant: ERMI, Inc., Atlanta, GA (US)

(72) Inventors: Thomas P. Branch, Atlanta, GA (US); Shaun K. Stinton, Chamblee, GA (US); Edward Dittmar, Marietta, GA (US); Nathaniel K. deJarnette, Lilburn, GA (US); T. Christopher Madden, Atlanta, GA (US)

(73) Assignee: RoboDiagnostics LLC, Atlanta, GA (US)

( * ) Notice: Subject to any disclaimer, the term of this patent is extended or adjusted under 35 U.S.C. 154(b) by 631 days.

(21) Appl. No.: 15/173,510

(22) Filed: Jun. 3, 2016

(65) Prior Publication Data
US 2017/0347942 A1 Dec. 7, 2017

(51) Int. Cl.
*A61B 5/00* (2006.01)
*A61B 5/11* (2006.01)
*A61B 34/10* (2016.01)
*A61B 34/20* (2016.01)

(52) U.S. Cl.
CPC .......... *A61B 5/4528* (2013.01); *A61B 5/1121* (2013.01); *A61B 5/4585* (2013.01); *A61B 5/702* (2013.01); *A61B 34/10* (2016.02); *A61B 34/20* (2016.02); *A61B 2034/107* (2016.02)

(58) Field of Classification Search
CPC ... A61B 5/4528; A61B 5/4585; A61B 5/1121; A61B 2034/107; A61B 34/10; A61B 34/20; A61B 5/702
See application file for complete search history.

(56) References Cited

U.S. PATENT DOCUMENTS

| 4,571,834 | A | * | 2/1986 | Fraser | A61B 5/1107 33/1 PT |
|---|---|---|---|---|---|
| 4,969,471 | A | | 11/1990 | Daniel et al. | |
| 5,935,086 | A | | 8/1999 | Beacon et al. | |
| 6,162,189 | A | | 12/2000 | Girone et al. | |
| 6,324,296 | B1 | | 11/2001 | McSheery et al. | |
| 7,291,119 | B1 | | 11/2007 | de Guise et al. | |
| 7,607,440 | B2 | | 10/2009 | Coste-Maniere et al. | |
| 8,170,716 | B2 | | 5/2012 | Coste-Maniere et al. | |
| 8,491,574 | B2 | | 7/2013 | Blumenkranz | |
| 8,571,710 | B2 | | 10/2013 | Coste-Maniere et al. | |
| 8,888,718 | B2 | | 11/2014 | Siston et al. | |

(Continued)

FOREIGN PATENT DOCUMENTS

| WO | 2014076147 A2 | 5/2014 |
|---|---|---|
| WO | 2015121830 A1 | 8/2015 |

*Primary Examiner* — Sean P Dougherty
(74) *Attorney, Agent, or Firm* — Lempia Summerfield Katz LLC

(57) ABSTRACT

A knee examination method includes situating a patient on a patient support adjacent a robotic knee testing apparatus, the apparatus having a motion tracking system. The robotic knee testing apparatus is set up including defining a world coordinate system based on a fixed location of a transmitter of the motion tracking system. The patient is set up including determining one or more local coordinate systems each based on setting up the patient and on one or more robot based points. The robotic knee testing apparatus is operable to manipulate a leg of the patient.

23 Claims, 17 Drawing Sheets

(56) References Cited

U.S. PATENT DOCUMENTS

| | | | |
|---|---|---|---|
| 2003/0018340 A1* | 1/2003 | Branch | A61B 17/3421 606/96 |
| 2003/0109780 A1 | 6/2003 | Coste-Maniere et al. | |
| 2004/0153191 A1* | 8/2004 | Grimm | A61B 34/20 700/114 |
| 2005/0119661 A1 | 6/2005 | Hodgson et al. | |
| 2005/0234332 A1 | 10/2005 | Murphy | |
| 2006/0161051 A1 | 7/2006 | Terrill-Grisoni et al. | |
| 2007/0015995 A1* | 1/2007 | Lang | A61B 5/1038 600/407 |
| 2007/0055176 A1 | 3/2007 | Branch et al. | |
| 2007/0088340 A1* | 4/2007 | Brock | A61B 34/70 606/1 |
| 2008/0154127 A1* | 6/2008 | DiSilvestro | G06K 9/32 600/427 |
| 2008/0208081 A1* | 8/2008 | Murphy | A61B 90/36 600/595 |
| 2009/0124936 A1 | 5/2009 | Branch et al. | |
| 2010/0010506 A1 | 1/2010 | Murphy | |
| 2010/0256504 A1* | 10/2010 | Moreau-Gaudry | A61B 8/08 600/476 |
| 2012/0046540 A1 | 2/2012 | Branch et al. | |
| 2012/0277634 A1* | 11/2012 | Proulx | G01C 25/005 600/595 |
| 2013/0041289 A1 | 2/2013 | Sena et al. | |
| 2013/0282024 A1 | 10/2013 | Blumenkranz | |
| 2013/0307955 A1 | 11/2013 | Deitz et al. | |
| 2014/0081181 A1 | 3/2014 | Branch et al. | |
| 2014/0135985 A1 | 5/2014 | Coste-Maniere et al. | |
| 2014/0222157 A1 | 8/2014 | Al Hares et al. | |
| 2014/0316242 A1 | 10/2014 | Musahl et al. | |
| 2015/0201867 A1 | 7/2015 | Peindl et al. | |
| 2015/0238276 A1* | 8/2015 | Atarot | A61B 1/00004 600/424 |
| 2015/0374446 A1* | 12/2015 | Malackowski | A61B 34/10 606/130 |
| 2017/0281281 A1* | 10/2017 | He | A61B 34/20 |
| 2017/0290631 A1* | 10/2017 | Lee | A61B 34/20 |
| 2018/0185100 A1* | 7/2018 | Weinstein | A61B 34/20 |

* cited by examiner

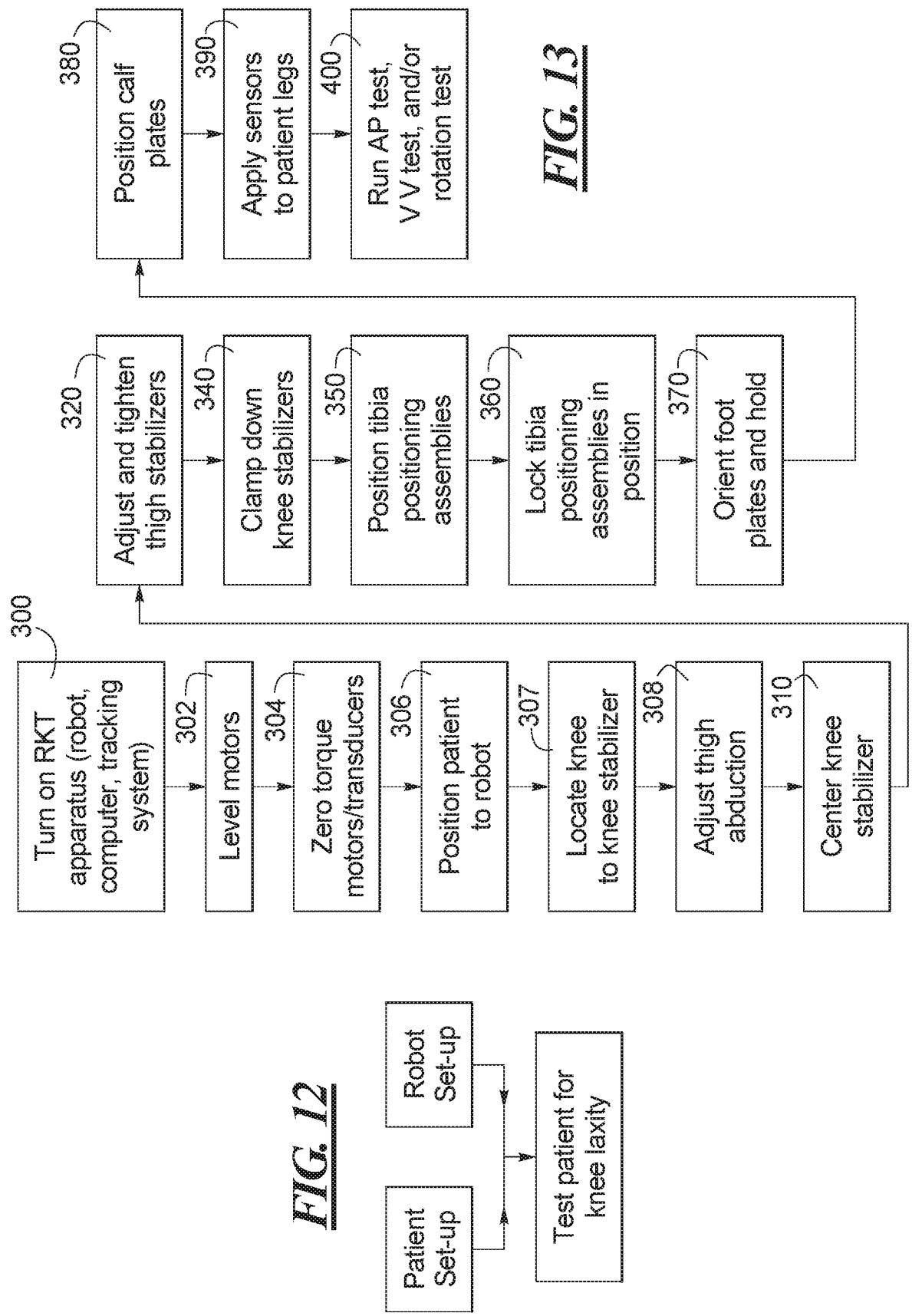

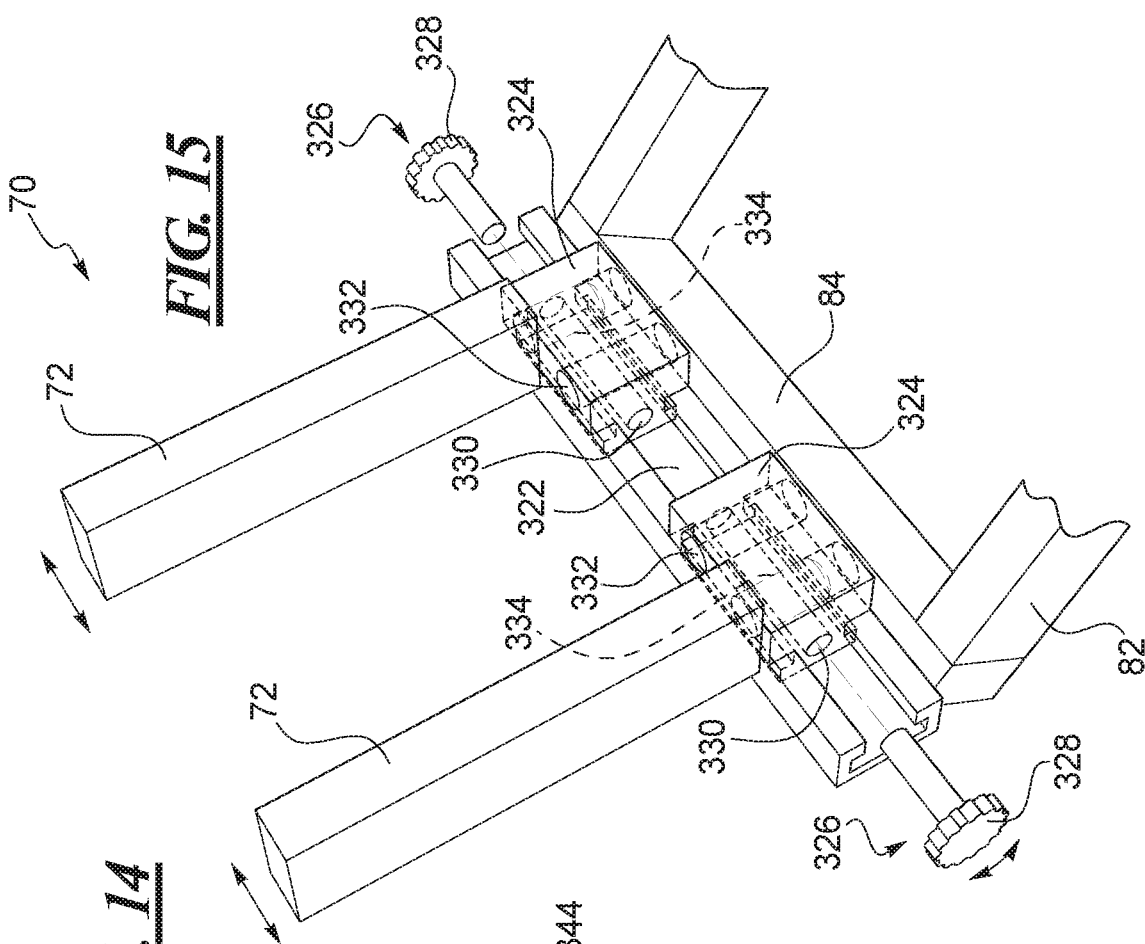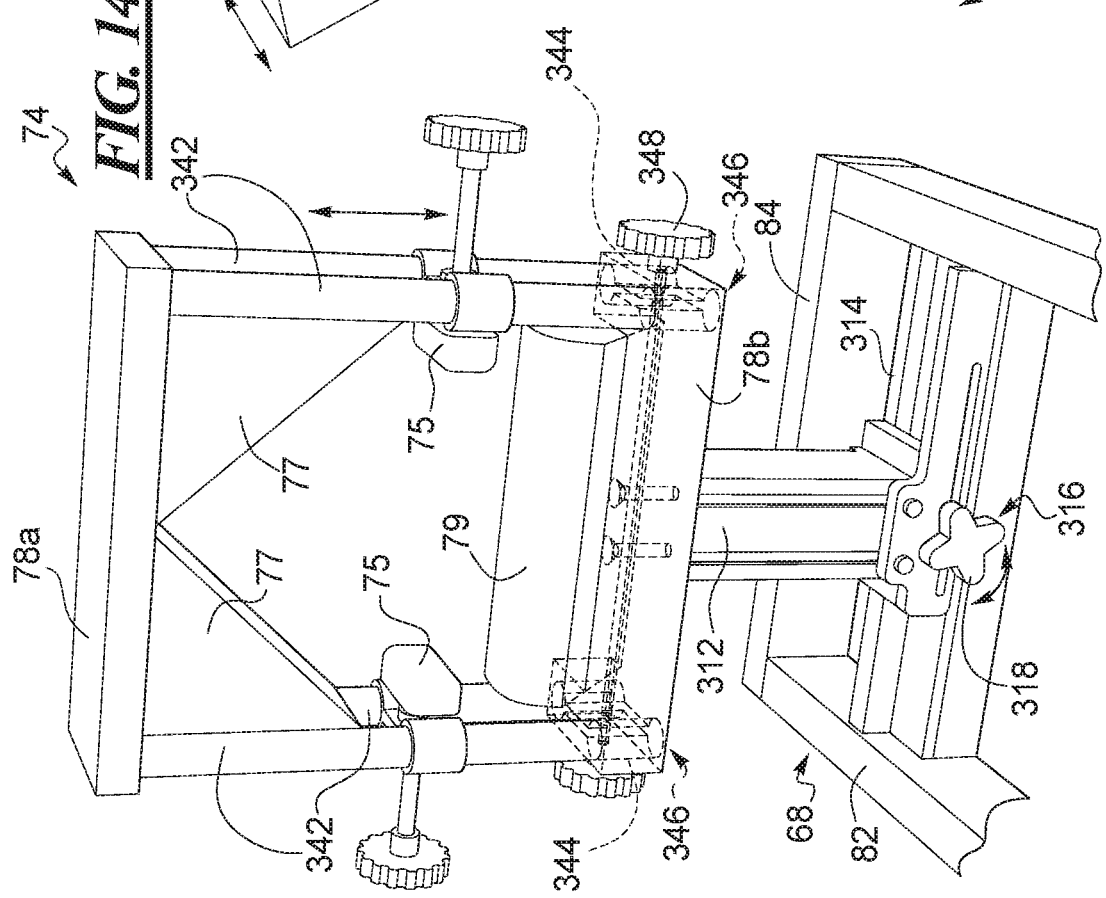

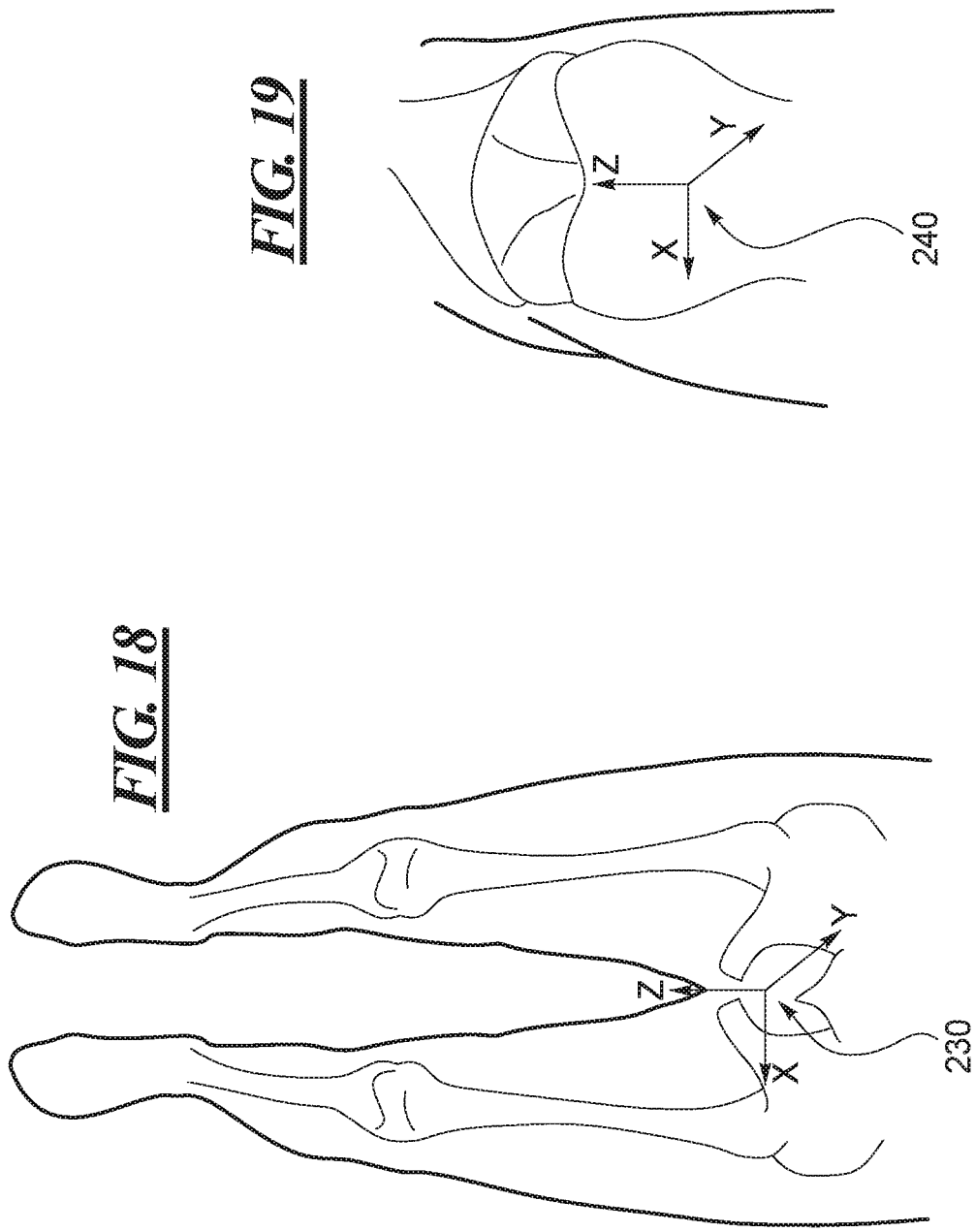

ROBOTIC JOINT TESTING APPARATUS AND COORDINATE SYSTEMS FOR JOINT EVALUATION AND TESTING

RELATED APPLICATION DATA

This application is related to the concurrently filed and commonly assigned applications entitled "Joint Play Quantification and Analysis", "Analysis System and Method for Determining Joint Equilibrium Position", "Biomechanical Characterization and Analysis of Joints", and "Robotic Knee Testing Apparatus and Patient and Apparatus Set-Up Methods", the entire disclosures of which are hereby expressly incorporated by reference.

BACKGROUND

1. Field of the Disclosure

The disclosure generally relates to joint evaluation using a robotic apparatus, and more particularly to coordinate systems of the apparatus or used by the apparatus for testing and evaluating joints of patients.

2. Description of Related Art

The knee joint is composed of the femur or thigh bone, the tibia or shin bone, and the patella or knee cap. The bones are connected by fibrous structures called ligaments, which allow a certain amount of "joint play" or motion to exist between the bone structures. When this joint play is increased or decreased, an abnormal or pathological condition exists in the knee. Attempts have been made in the past to quantify this increase or decrease in joint play of the knee with limited success.

Knee injuries often cause damage to one or more of the structures that form the knee joint. Such injuries typically cause an increase in joint play or motion of the knee. A patient may interpret an increase in joint play as a sensation that the knee is slipping or coming out of joint. In other words, this sensation may be described by the patient as the feeling of joint instability. Knee instability may be related in part to an increase in the length of the ligaments that connect the bones together, an increase or change in compliance (elastic resilience or stretchiness) of the ligaments, or both. Knee instability may also be related in part to the shape and size of the joint bones. The degree or likelihood of the knee joint bones actually coming out of joint or becoming unstable is related to the amount of stretch or increased length of each knee ligament, the number of knee ligaments involved, and the existence of damage to one or more other support structures of the knee joint, such as the joint bones themselves, the menisci, or the like. Accurate measurement of an increase in ligament length can be critical to restoring a patient's injured or damaged knee to as close as possible to its original functional and anatomical structure and condition.

For the most part, knee injuries and ligament damage have been diagnosed using only manual tests. These tests are performed by doctors or other medical personnel, i.e., clinicians, on the patient in order to detect and measure joint play to diagnose damage to the knee ligaments or other knee joint support structures. There are a number of commonly known manual tests used to evaluate increased joint play that is usually associated with an anterior cruciate ligament (ACL) tear. These tests include the Lachman test, the Pivot Shift test, and the Anterior Drawer Test. Additional manual tests are known for evaluating other ligament injuries in the knee. These tests include the dial test and the Varus-valgus test. Because all of these tests are performed manually by individual medical personnel, these tests naturally are limited by the specific clinician's subjective evaluation. The subjective nature of the tests may hinder the precision or accuracy of any diagnosis of the extent of ligament lengthening, the change in ligament compliance or elastic resilience, i.e., stretchiness, or combinations thereof.

The Lachman test is performed with a patient lying in a supine position. The clinician will bend the patient's knee joint at approximately 20 to 30 degrees. The clinician places one hand on the patient's upper thigh and their other hand below the upper part of the patient's calf. The clinician then applies upward pressure under the patient's calf and downward pressure on the patient's thigh. The clinician further applies downward pressure on the patient's lower leg and upward pressure on the patient's thigh. These maneuvers induce anterior-posterior translation between the patient's femur and tibia. The degree of translation is subjectively determined by the clinician to diagnose the injury or joint damage.

The dial test, or the 30 degree tibial axial rotation test, is performed with the patient lying in the supine position with the knee flexed at 30 degrees and the heel on the table. The foot is rotated in maximum internal rotation followed by maximum external rotation. The amount of rotation occurring both at the proximal tibia and at the foot is noted.

The Varus-valgus stress test can be performed under many conditions, the most common one having the patient supine and the lower leg cradled in the clinician's arms. Pressure is applied in an abduction and adduction movement at the foot while a hand stabilizes the femur. An assessment of both motion and separation of the joint space is noted along its medial and lateral joint line.

The Anterior Drawer test is also performed with the patient lying in a supine position, but with the knee joint bent to about 90 degrees (x-axis rotation). The patient's foot is supported by a table or chair while the clinician applies hand pressure to the knee joint. The Anterior Drawer test is subjectively graded by the clinician based on the perceived amount or extent of anterior translation of the tibia with respect to the femur.

The Pivot Shift test may be considered to combine some or all of the foregoing tests into a complex maneuver. The Pivot Shift test is similarly performed with the patient lying in a supine position. The leg is straightened out so that the knee joint is placed in full extension (x-axis rotation). A valgus or side-to-side outward rotation (y-axis rotation) force and an internal or twisting rotation (z-axis rotation) force is applied to the knee to allow the lateral tibia to slip anteriorly from underneath the lateral femoral condyle. As the knee is flexed or bent (x-rotation), the tibia is allowed to slip suddenly back underneath the femoral condyle. The clinician subjectively determines whether there is an abnormal external rotation (z-axis rotation) and posterior translation (y-axis translation) of the tibia with respect to the femur. The degree of shift that is felt or determined by the clinician represents to the clinician the relative increased translation (y-axis translation) of the lateral side of the knee with respect to the increased translation (y-axis translation) of the medial side of the knee. A sudden shift in the knee joint is felt by the clinician and represents the point at which the tibia bone slides from in front of the radius of curvature of the curved end of the femur back to its normal position under the femoral condyle. The Pivot Shift test is inherently subjective, difficult to accurately perform, difficult to teach, and ultimately difficult to quantify.

Grading each test usually involves the opinion of the physician placing the test into one of three categories, such as Grade I, Grade II, or Grade III. For the Pivot Shift test, the grading depends upon the speed and intensity of the knee joint slipping back into place. For other tests, the grading represents the amount of motion detected by the clinician during the examination. For example, Grade I may be used to represent 0-5 mm of joint play. Grade II may be used to represent 6-10 mm of joint play. Grade III may be used to represent 11-15 mm of joint play. The clinician then subjectively rates the pivot shift as Grade I, Grade II, or Grade III depending upon the degree of rotational and translational shift felt during the test.

For a ligament injury to be diagnosed, the result of one or more of these tests is considered abnormal, suggesting a Grade II or more increase in joint play. In the past, the results of a single test were used to diagnose a ligament tear. Often this "one dimensional" diagnosis would result in a surgical procedure. For instance, in order for a clinician to diagnose an injured ACL using the aforementioned manual tests, the clinician determines whether the knee feels abnormal. The accuracy of an ACL injury diagnosis provided by a clinician using currently known manual tests depends on the skill and experience of the clinician and their subjective determinations. A misdiagnosis can lead to unnecessary treatment or unnecessary delay in treatment, which may result in an increased risk for further injury or damage to the patient's knee joint.

Combinations of these clinical examination tests can be used to diagnose lateral collateral ligament (LCL), medial collateral ligament (MCL), posterior cruciate ligament (PCL), and other knee ligament injuries. Each manual test relies on grading the degree of length (or damage) increase in the ligament based on relative increase in joint play into three Grades or categories. There is no effort to grade the compliance or elastic resilience, i.e., stretchiness, of the ligaments using these manual tests. An expert clinician may instead describe the ligament in terms of its subjective feel to the clinician, such as by determining that the joint has a hard or soft endpoint. Also, a knee joint may have injury or damage to more than one ligament or structure. The more ligaments and structures of the knee joint that are damaged, the more complex it is for the clinician to perform a manual knee examination. This can make the full diagnosis less accurate and less precise.

Clinicians and surgeons manually examine the injured knee joint for altered or increased joint play. However, due to the variability in size of the patient, size and experience of the surgeon, and the potential degree or subtlety of an injury, consistent and reproducible reports of joint play between surgeons is not possible. Many reports have documented that, whether diagnosis is performed manually or even with manual arthrometers, the manual application of torque to the knee joint varies widely between clinicians. This results in inconsistencies in the examination of joint play and, ultimately, the diagnoses made by clinicians.

Others have attempted to reduce the manual nature of such joint tests and to instrument the knee joint during testing. The objective has been to mechanically or objectively quantify or measure a change in the structure of the knee after ligament damage. Several devices have been developed in attempting to more accurately quantify the extent of injury or relative displacement and compliance of a ligament in the knee. In one example, such devices have been developed by Medmetric Corp. These devices include the KT-1000 and KT-2000 models. The KT devices are intended to measure the anterior-posterior translation of the tibia with respect to the femur. These KT devices attach to the patient's tibia during testing.

These KT devices attempt to quantify the findings achieved by a clinician performing the Lachman test and the Anterior Drawer Test. Force is applied to a handle on the device, which measures the force and delivers the amount of applied force to the clinician using sounds, such as a low pitched sound for a 15 pound force and a higher pitched sound for a 20 pound force. The applied force in the KT devices pulls anteriorly along the y-axis through a strap that wraps underneath the patient's calf. The translation is determined using a technique that measures the relative motion between a pad placed against the anterior tibia and a pad placed against the patella. The KT devices do not measure relative displacement or compliance in any of the other degrees of freedom in the knee. Also, quantified results from using the KT-1000 or KT-2000 devices have been found to have no correlation with patient satisfaction. In contrast, the subjective Pivot Shift test has been shown to be correlated with patient satisfaction.

Other devices are also known and include the Stryker KLT, the Rolimeter, the Rotameter, and the KSS system. These known devices use similar mechanisms to attempt to quantify the normal amount of joint play or motion between the femur and tibia in the knee joint, as well as any increased joint play or motion in the joint associated with ligament lengthening and damage. The applicant of the instant application has developed robotic knee testing (RKT) apparatuses, the basics of which are disclosed and described in U.S. publication nos. 2012/0046540 and 2014/0081181. The apparatus utilizes motors to perform knee movements during testing and sensors to measure degree of relative movement of the structures in the knee joint. Portions of the knee and leg can be stabilized or moved, as needed during testing.

Past methods of knee laxity testing in the past, both manual and instrumented, have a well-documented history of inaccuracy and inconsistency, both when testing the same patient from day to day and when two different examiners test the same patient. This is in part due to 1) the subjective nature, among examiners and among patients, of these prior examination and diagnosis techniques, 2) the complexity of the anatomy of the knee, 3) the lack of a system or method that is reliably repeatable to measure knee laxity, and 4) the accumulation of error that is introduced at different stages of an examination or diagnosis that is inherent in these prior known instruments and procedures. Multiple studies have brought into question the reproducibility and reliability of both the aforementioned manual knee exam techniques and the above-noted existing devices designed to simulate knee examinations. Many of these issues can be attributed to an inconsistent set-up of the exam or device, each of which can lead to inconsistent initial conditions at the start of the test and inaccuracies throughout the testing.

Introducing significant error at any one or more steps during a test can greatly affect, and invariably reduce, the accuracy of the ultimate diagnosis. The degree of error may often overwhelm the ability to obtain an accurate diagnosis. This is because, at every step of the testing and evaluation process, relatively small motions or movements are being detected, measured, and evaluated. Instrumented devices were developed as attempts to make measuring knee laxity or joint play more consistent and to try and reduce the degree of error involved, both in patient set-up and in testing the patient. However, these devices still typically rely on the examiner to determine the zero point or neutral position of the knee and/or require the examiner to manually apply the forces to the knee during testing and evaluation. These issues with existing instrumented devices lead to substantial inconsistency in the results.

Prior solutions have struggled to define a zero point or neutral position in the joint for each type of movement. Also, for rotation, prior solutions poorly distinguish between internal and external rotation. As a result, internal and external rotation have been typically combined into one single measurement. Further, when measuring AP translation, the KT-1000 relies on the tester to pull the tibia into anterior translation manually using a beeper to denote different force levels. The KT-1000 has a plastic mount that is designed to set the knee in the optimal testing position, but the manual aspect of the device provides for an inherent amount of error in the test.

SUMMARY

In one example according to the teachings of the present disclosure, a knee examination method includes situating a patient on a patient support adjacent a robotic knee testing apparatus having a motion tracking system. The method includes setting up the robotic knee testing apparatus including defining a world coordinate system based on a fixed location of a transmitter of the motion tracking system. The method includes further setting up the patient including determining one or more local coordinate systems each based on setting up the patient and on one or more robot based points. The method also includes operating the robotic knee testing apparatus to manipulate a leg of the patient.

In one example, the step of setting up can further include a step of securing at least a first sensor of the motion tracking system to a first tibia of the leg of the patient whereby the first sensor can be used to define a first local coordinate system for the tibia.

In one example, the step of setting up can include securing a first circular sensor of the motion tracking system to a first tibia of the leg of the patient to define a first local coordinate system for the tibia.

In one example, the step of setting up can include securing a first circular sensor of the motion tracking system to a first tibia of the leg of the patient to define a first local coordinate system for the first tibia and securing a second sensor of the motion tracking system to a second tibia of a second leg of the patient whereby the second sensor is used to define a second local coordinate system for the second tibia.

In one example, the step of setting up can include identifying and recording one or more anatomical points on the leg of the patient using a pointer having a sensor of the motion tracking system. The one or more anatomical points can be used to define the one or more local coordinate systems.

In one example, the method can include identifying and recording one or more anatomical points on the leg of the patient using a pointer with a sensor of the motion tracking system, the one or more anatomical points including one or more of a tibial tubercle, a midpoint between a medial tibial plateau and a lateral tibial plateau, a medial-lateral midpoint of an anterior proximal tibia and posterior proximal tibia, and a midpoint of a medial malleolus and a lateral malleolus of the leg.

In one example, wherein the step of examining can include calculating a relationship between a coordinate system determined using one or more bony landmarks or anatomical points on the leg of the patient and using the world coordinate system.

In one example, wherein, in the step of setting up, the motion tracking system can be an electromagnetic tracking system.

In one example, the method can include the step of capturing motion data of the leg and can include assessing the motion date relative to the world coordinate system.

In one example, the method can include the step of capturing motion data of the leg and can include assessing the motion data relative to the one or more local coordinate systems.

In one example, the method can include the step of capturing motion data of the leg and can include assessing the motion data relative to both the world coordinate system and the one or more local coordinate systems.

In one example, the step of further setting up can include the step of defining a robot based femoral coordinate system for the leg of the patient including marking one or more fixed points on a knee stabilizer of the robotic knee testing apparatus.

In one example, the method can include the step of defining a robot based femoral coordinate system including marking one point at a midpoint of a knee stabilizer above the knee and marking two points laterally spaced apart on the knee stabilizer below the knee.

In one example, the method can include performing each of the steps of setting up the robotic knee testing apparatus, further setting up the patient, and operating the robotic knee testing apparatus for both legs of the patient.

In one example, the method can include the step of obtaining data for a world view perspective for each leg of the patient using the world coordinate system and also obtaining data for a local perspective for each leg using the one or more local coordinate systems.

In one example, step of further setting up the patient can include defining a tibial coordinate system of the one or more local coordinate systems for the leg using the motion tracking system whereby a Z axis of the tibial coordinate system can extend in a direction of a tibia of the leg.

In one example, the method can include a step of defining a tibial coordinate system, which can include defining an origin of the tibial coordinate system as a midpoint between points taken on a medial tibial plateau and a lateral tibial plateau of the leg.

In one example, the method can include the step of defining an origin of a tibial coordinate system and can include adjusting the origin anteriorly or posteriorly to a midpoint of a thickness of proximal end of the tibia.

In one example, the step of further setting up the patient can include defining a femoral coordinate system of the one or more local coordinate systems for the leg using the motion tracking system whereby a Z axis of a tibial coordinate system is also used as a Z axis of the femoral coordinate system.

In one example, the step of further setting up the patient can include defining a femoral coordinate system of the leg using the motion tracking system whereby an origin of the femoral coordinate system is central to a triangle defined by taking three points on a portion of the robotic knee testing apparatus surrounding the knee of the leg.

In one example, the method can include a step of defining a femoral coordinate system by taking three points on a knee stabilizer holding the knee of the patient in a substantially fixed position.

In one example, the method can include a step of defining a femoral coordinate system having a Z axis of a femur of the leg that is parallel to an epicondylar axis of the femur.

In one example according to the teachings of the present disclosure, a knee examination method includes situating a patient on a patient support adjacent a robotic knee testing apparatus. The method includes setting up the robotic knee testing apparatus including defining a world coordinate system based on a fixed location of a transmitter of a motion tracking system. The method further include setting up the patient including determining one or more local coordinate systems each based on selected anatomical points on a leg of the patient and on one or more robot based points. The method also includes operating the robotic knee testing apparatus to manipulate a leg of the patient.

In one example according to the teachings of the present disclosure, a method of setting up a patient and a robotic knee testing apparatus to examine the knees of the patient includes situating the patient on a patient support adjacent the robotic knee testing apparatus. The method includes holding each knee of the patient using a respective knee stabilizer of the robotic knee testing apparatus. The method also includes restraining each thigh of the patient using a respective thigh stabilizer of the robotic knee testing apparatus. The method includes defining a world coordinate system based on a fixed location of a transmitter of a motion tracking system. The method also includes setting up the legs of the patient relative to the robotic knee testing apparatus in part by determining one or more local coordinate systems each based on one or more robot based points on the robot determined using sensors in communication with the transmitter.

In one example, the method can include the step of adjusting portions of a drive system of the robotic knee testing apparatus to a zero torque or neutral position relative to each knee of the patient.

BRIEF DESCRIPTION OF THE DRAWINGS

Objects, features, and advantages of the present invention will become apparent upon reading the following description in conjunction with the drawing figures, in which:

FIG. 12 shows a flow chart of one example of a set-up method according to the teachings of the present disclosure.

FIG. 13 shows a flow chart of one example of a set-up method according to the present disclosure.

FIG. 14 shows one of a knee stabilizer for the robot of the RKT apparatus of FIG. 1.

FIG. 15 shows one example of a thigh stabilizer for the robot of the RKT apparatus of FIG. 1.

FIG. 18 shows one example of a world coordinate system defined by the analysis system of FIG. 11.

FIG. 19 shows one example of a local coordinate system defined by the analysis system of FIG. 11.

Figure 1:
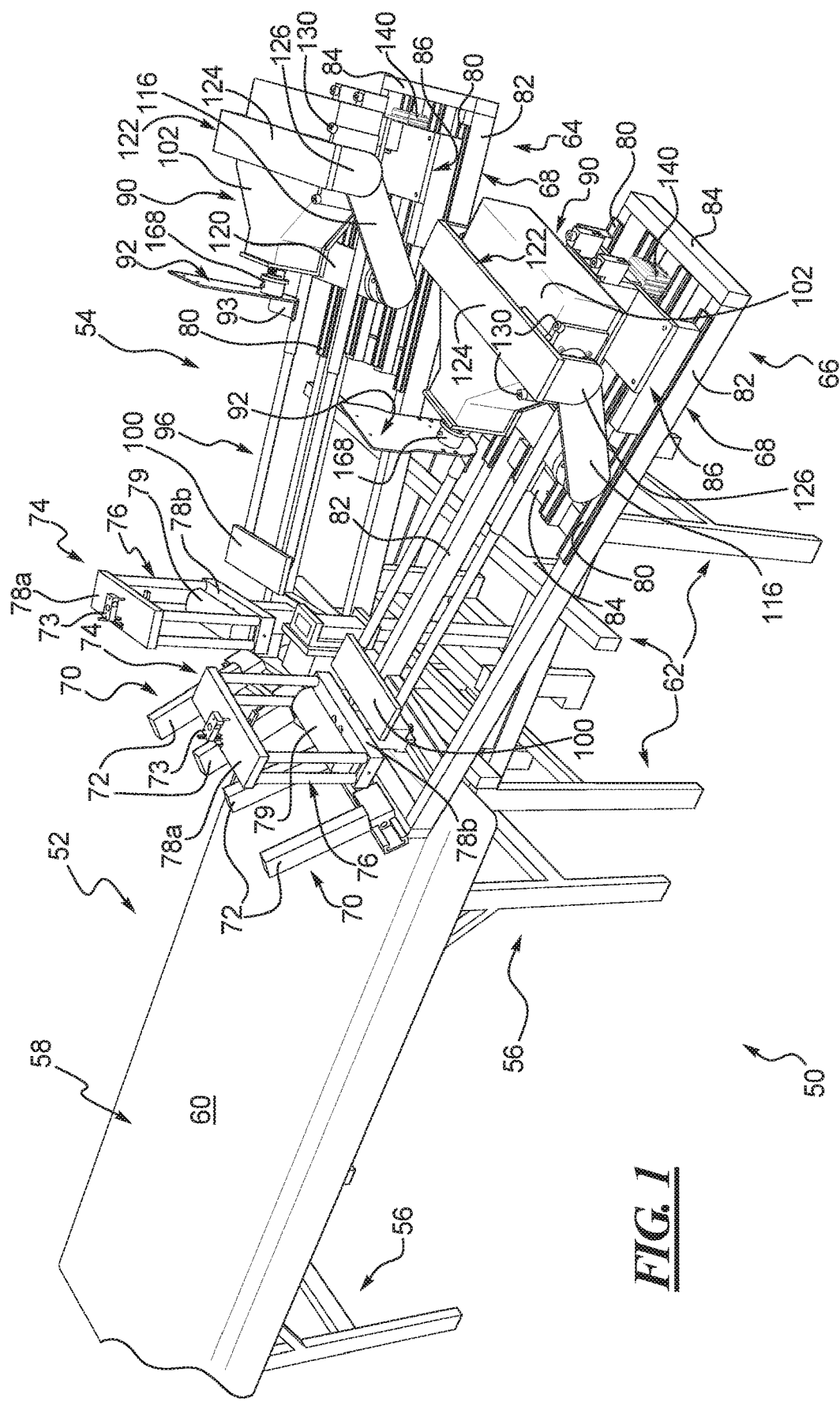
FIG. 1 shows a perspective view of one example of a robotic knee testing or RKT apparatus according to the teachings of the present disclosure.

The disclosed methods, systems, and devices may assume various forms. Specific examples are illustrated in the drawing (and are hereafter described) with the understanding that the disclosure is intended to be illustrative, and is not intended to limit the invention to the specific examples described and illustrated herein.

DETAILED DESCRIPTION OF THE DISCLOSURE

Systems and methods involving quantification and analysis of joint equilibrium position, patient and equipment set-up, initial conditions, zero point or neutral position for the patient and the equipment, and coordinate systems for the patient and the equipment are described herein. Although described in connection with a number of examples involving knee testing and evaluation, the disclosed systems and methods are not limited to a particular type of joint. The systems and methods are also not limited to particular types of tests. The nature of the tests may vary considerably in conjunction with the type of joint being assessed or evaluated. The data from any number of tests may be combined or synthesized.

Although described in connection with a number of examples of a robotic knee testing apparatus, the source of the data obtained by the disclosed systems and methods may vary. A variety of different test apparatuses, devices, and equipment may be used in conjunction with, and/or as part of, the disclosed systems and methods. As described below, the nature of the data acquired by the test equipment may vary as well.

To accurately measure the motion of bones relative to one another, the present disclosure involves defining coordinate systems that are optimized to the kinematic methods being used. Anatomically relevant coordinate systems may be preferred, but depending on the system being used, it can be hard to accurately and consistently pick anatomical points as references for the various coordinate systems. Others have used electromagnetic tracking systems and anatomically based coordinate systems, but not to the extent, for the purposes, and in the manner disclosed herein.

Further, the disclosed methods yield a consistent set-up for the tests that is specifically designed to improve upon reliability and consistency in the testing procedures and to ensure consistent and accurate examinations and diagnoses. The concepts of initial conditions, zero point or neutral position, equilibrium position, and new extent are employed for the disclosed systems and methods, also to improve upon reliability, accuracy, and consistency in the testing procedures, examinations, and diagnoses.

In one example, the disclosed RKT apparatus and various systems and methods are intended to aid in producing a more consistent set-up at the start of a test procedure on a knee or knees of a patient using the RKT apparatus. The disclosed systems and methods are in turn intended to significantly reduce error that may otherwise be introduced into the tests, test results, and data. The disclosed systems and methods can thus yield more consistent and accurate test results. These and other objects, features, and advantages of the present inventions will become apparent to those having ordinary skill in the art upon reading this disclosure.

Turning now to the drawings, FIG. 1 shows one example of a RKT apparatus 50 that has been developed by the applicant and assignee of the present inventions that are disclosed and described herein. Specific details of the RKT apparatus 50 are more fully disclosed and described in the above-noted U.S. publication no. 2014/0081181, also owned by the applicant and assignee of the invention disclosed herein. Specific details of the overall function and operation of the RKT apparatus are described in both the above-noted U.S. publication no. 2012/0046540 and the '181 publication. The entire content of both of the '181 and '540 publications are hereby incorporated herein by reference.

The RKT apparatus 50 of FIG. 1 generally has a patient support, i.e., a table assembly 52. The RKT apparatus 50 also has a robotic mechanism or limb manipulation device, identified for ease of description herein as a robot 54, positioned at one end or edge of the table assembly. The table assembly 52 in this example has a supporting frame that is identified herein as a base 56 beneath a patient platform 58. The base 56 is configured to rest on a floor or surface and to support the patient platform 58 above the floor. The patient platform 58 can include a substantially rigid or sturdy panel (not shown) capable of holding and supporting a patient thereon. The panel can be affixed to or otherwise supported by the base 56. The panel of the patient platform 58 can underlie a padded surface 60, which can include a textile or fabric material that covers a cushion, padding, or the like (also not shown).

As will be evident to those having ordinary skill in the art, the configuration and construction of the table assembly 52 can vary considerably from the example disclosed, illustrated, and briefly described herein. The base 56 and/or the patient platform 58 can each be altered in size, shape, orientation, height, construction, materials, and the like. The base can include multiple legs and frame elements that are assembled or connected to one another, as in the illustrated example. Alternatively, the base can be formed as one unitary support element. The patient platform can also be formed of multiple components and can be fastened to or otherwise attached to the base. Alternatively, the patient platform can an integral, one piece fabricated structure and can be fabricated as part of the base or attached thereto. The table assembly need not be a table, but instead can be a chair, a suspension system, or other suitable patient support that is capable of properly positioning and retaining a patient relative to the robot 54 for testing and examination. The table assembly 52 can further include additional features, though not disclosed or described herein, that may be used to assist in positioning a patient on the platform, to assist in maintaining a patient's position on the platform, or to otherwise enhance patient comfort or improve performance of the table assembly, the RKT apparatus, or both.

With reference to FIG. 1, the robot 54 in this example can include a main or primary support frame structure, identified herein for ease of description as a frame 62. The frame 62 may optionally be coupled to, a part of, or otherwise supported by or connected to a portion of the base 56 of the table assembly 52, as shown in FIG. 1. Alternatively, the frame of the robot 54 can be an extension of, connected to, or otherwise supported by a portion of the patient platform 58. In a further alternative, the frame can be some combination of such supporting structures and arrangements or can be a completely separate structure. In any case, the frame 62 in this example supports and positions the robot 54 of the RKT apparatus 50 at one end of the table assembly 52.

Figure 2:
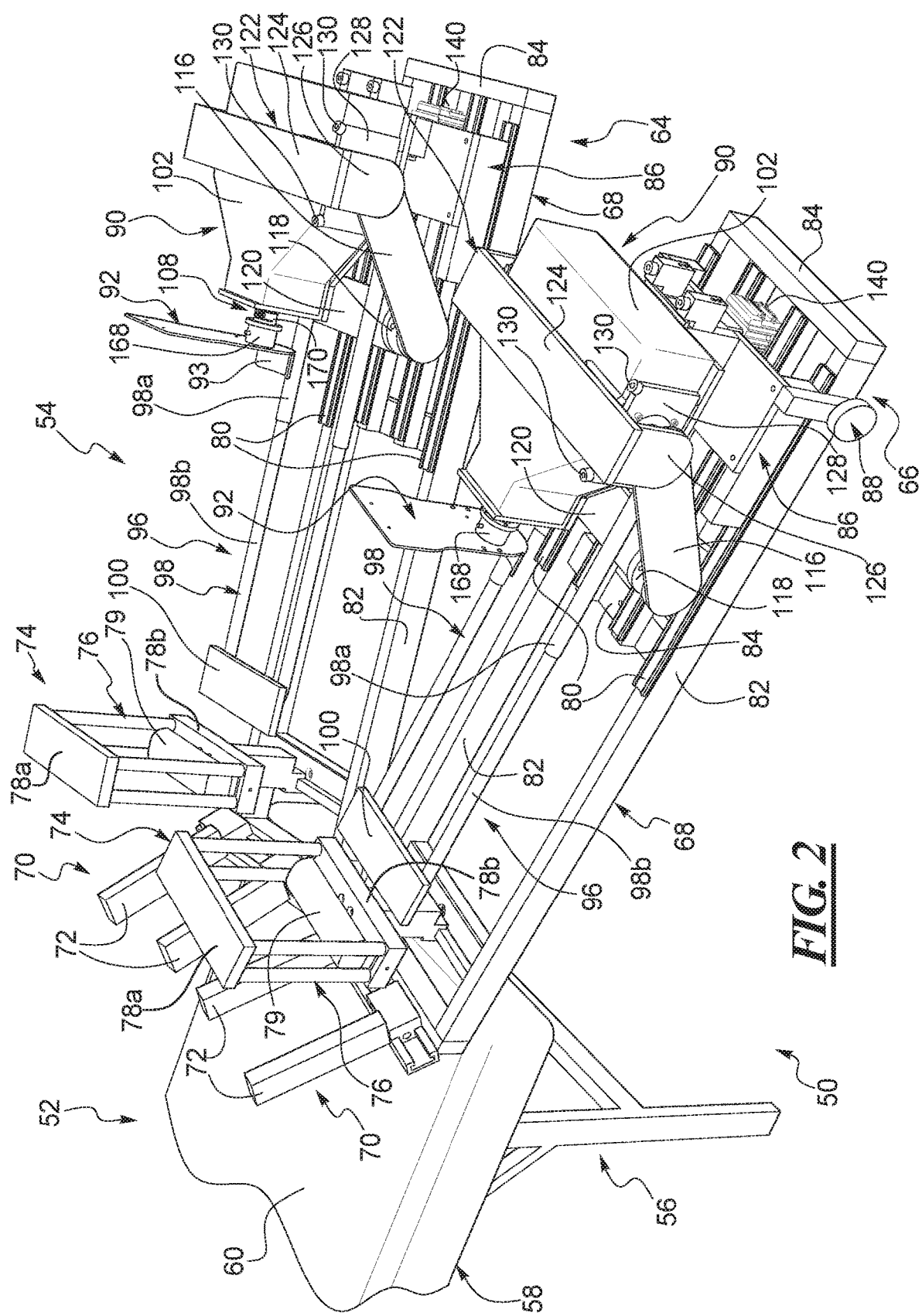
FIG. 2 shows an enlarged view of a limb evaluation device or robot of the RKT apparatus of FIG. 1.
Figure 3:
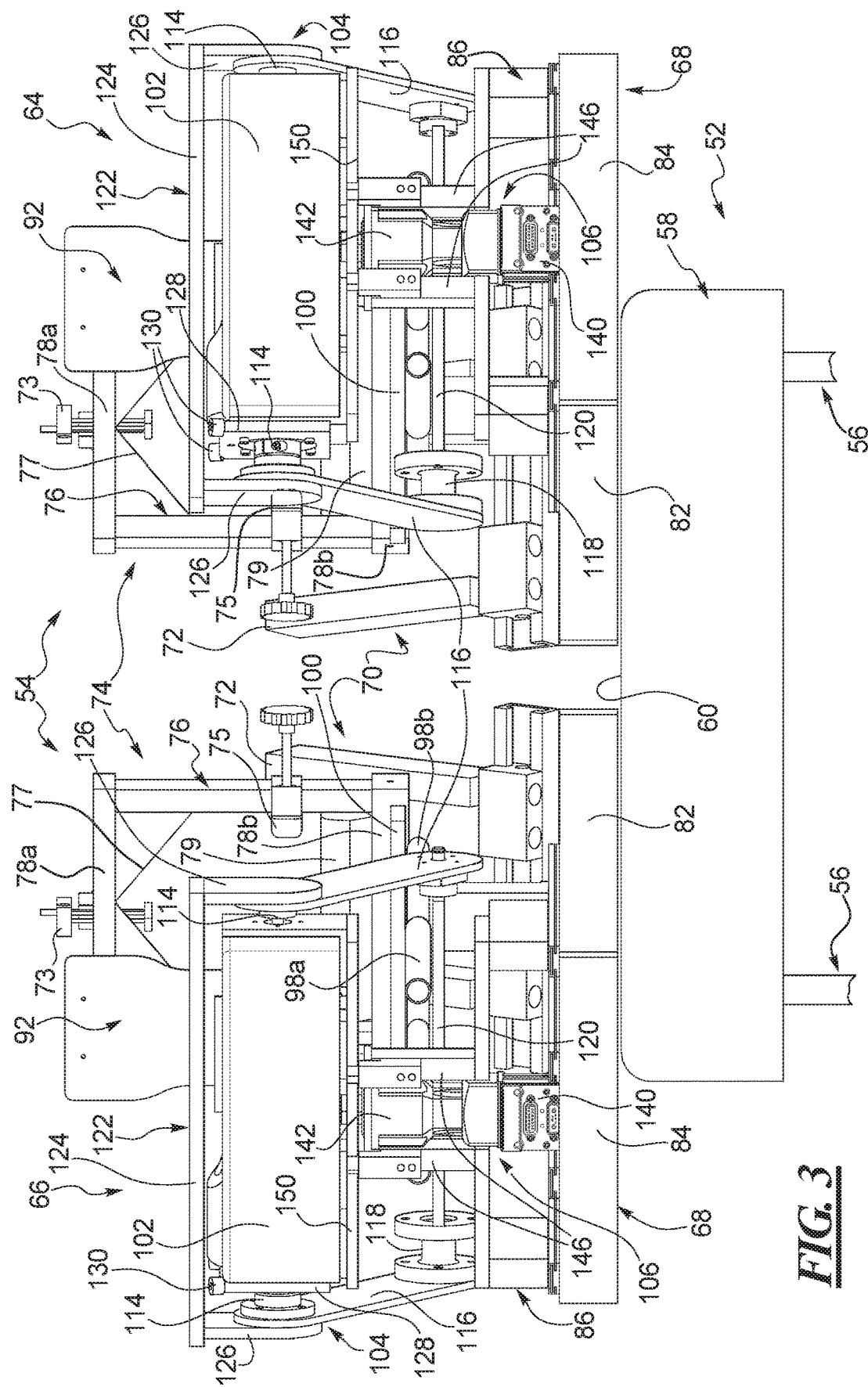
FIG. 3 shows an end view of the robot when viewed from the right hand side in FIG. 2.

In the disclosed example and with reference to FIGS. 2 and 3, the robot 54 has a left leg testing and evaluation mechanism and a right leg testing and evaluation mechanism, each mechanism respectively identified herein as a left leg portion 64 and a right leg portion 66 of the robot. The left and right leg portions 64, 66 have substantially the same construction, and may be essentially identical, if desired, and each is constructed to support and evaluate a left leg and right leg, respectively, of a patient. Therefore, like reference numerals are used herein to identify common parts of each of the two leg portions 64, 66 that have the same construction. The left and right leg portions 64, 66 each have a sub-frame 68 that, in this example, is supported by the frame 62 of the robot 54. Each sub-frame 68 supports the components and parts of the corresponding left and right leg portions 64, 66. For ease of description, the right leg portion 66 of the robot 54 is described in more detail below with the understanding that the left leg portion 64 has or may have the same overall construction. Differences between the two leg portions are identified herein, if and as needed. It is possible that an RKT apparatus is provided that has only one leg portion for evaluating only one leg of a patient at a time. However, in the disclosed example, the RKT apparatus 50 has left and right leg portions 64, 66.

Figure 4:
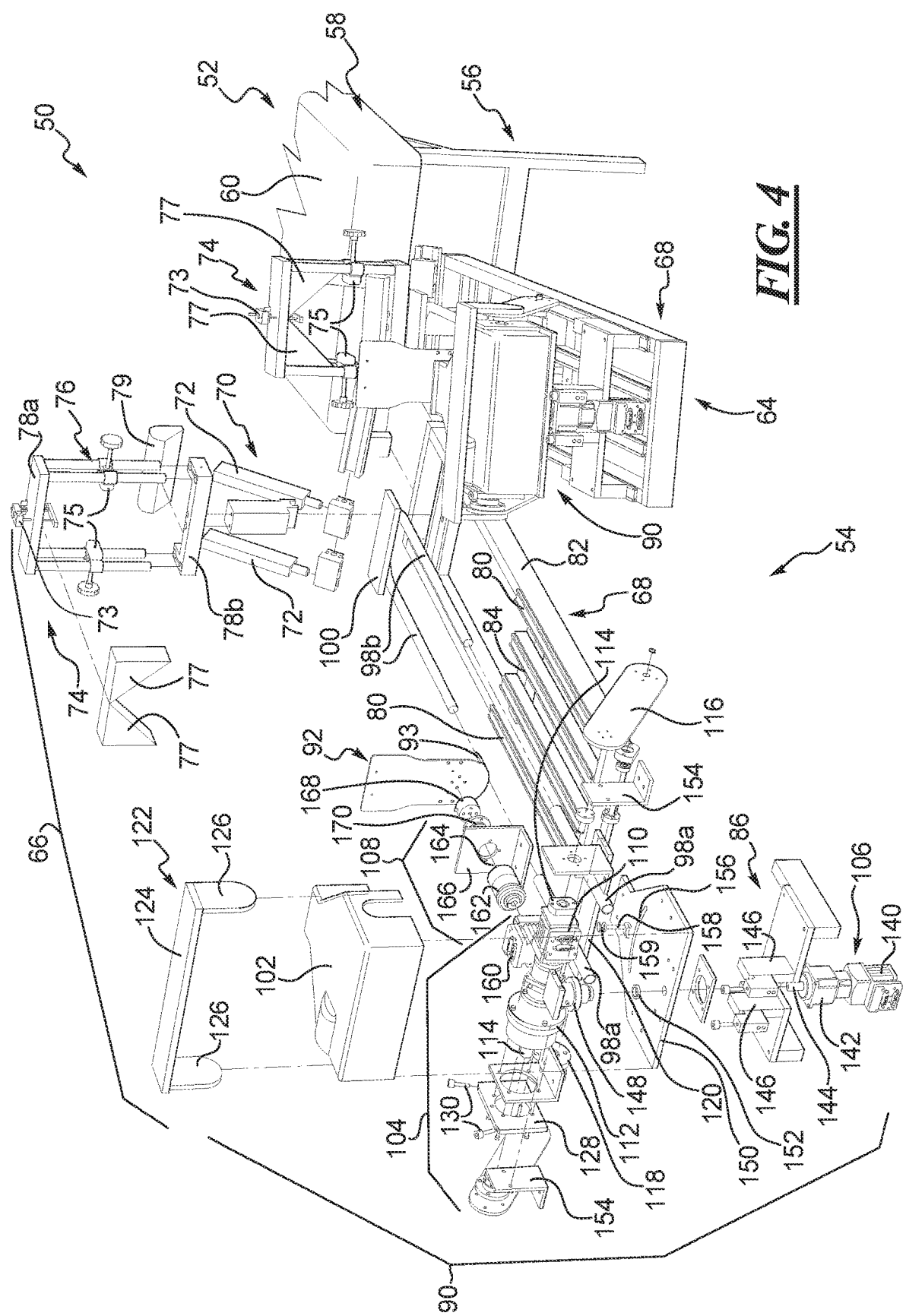
FIG. 4 shows a partial exploded view of the robot of FIG. 2 with the right leg portion of the robot exploded.
Figure 5:
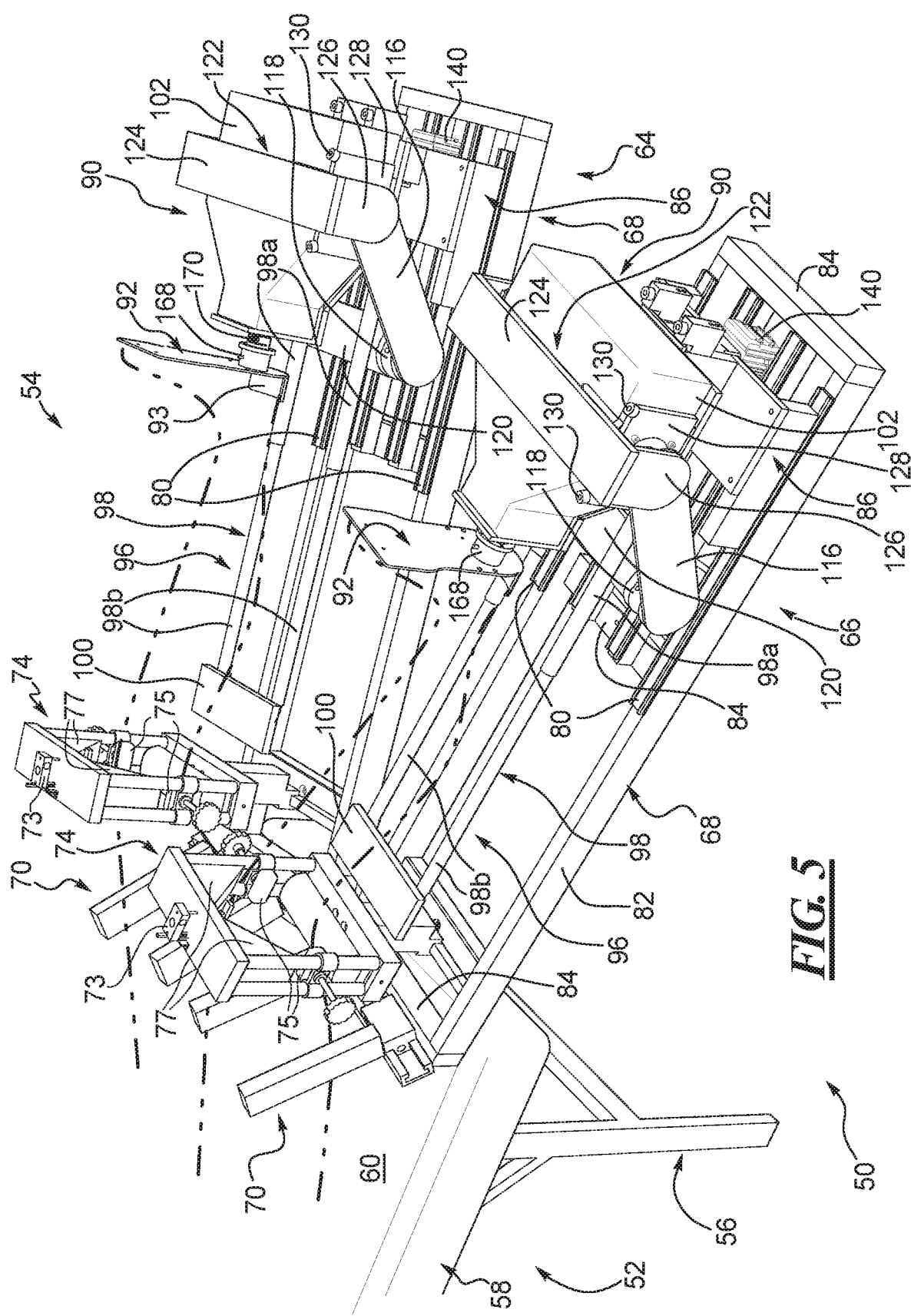
FIG. 5 shows the robot of FIG. 2 and depicts left and right legs of a patient positioned relative to the left and right leg portions of the robot.

As depicted in FIGS. 2-4, the right leg portion 66 has a thigh stabilizer 70 positioned closest to the table assembly 52. The thigh stabilizer 70 can be mounted to the frame 62 or the sub-frame 68, or can be otherwise mounted to a portion of the RKT apparatus 50 in a manner suitable for use as described below. The thigh stabilizer 70 can be constructed so as to be positionally adjustable to accommodate a wide range of patients of different size. Alternatively, the thigh stabilizer 70 can be mounted in a fixed position relative to the table assembly 52, whereby the position of the patient on the table assembly 52 and relative to the thigh stabilizer 70 might be adjustable. In either embodiment, the thigh stabilizer 70 should be positioned or positionable to contact a portion of a patient's upper leg or thigh above the knee, as depicted in FIG. 5.

The thigh stabilizer 70 in this example has a pair of femur clamping elements 72, i.e., medial and lateral clamping elements that are laterally spaced apart and width-wise adjustable relative to one another. Though not shown herein, the clamping elements can include a pad or pads on the thigh facing surfaces, if desired, to provide a degree of comfort for a patient. The femur clamping elements 72 can be side-to-side adjusted in order to clamp or otherwise securely hold a patient's right femur and thigh in a substantially fixed side-to-side position during testing, evaluation, or treatment, as described below. If the thigh stabilizer 70 is positionally adjustable, it should be capable of being secured in a fixed selected position, once properly adjusted for a given patient, relative to the table assembly 52 and/or robot 54 during testing, evaluation, or treatment. The configuration and construction of the thigh stabilizer 70 can vary considerably from the example shown herein. The clamping elements 72 can be replaced by other suitable securing or clamping devices or elements and the mechanisms to adjust and secure the thigh stabilizer 70 can also vary.

The right leg portion 66 also has a knee stabilizer 74 positioned adjacent the thigh stabilizer. The knee stabilizer 74 can also be mounted to the frame 62 or the sub-frame 68, or can be otherwise mounted to a portion of the RKT apparatus 50 in a manner suitable for use as described below. The knee stabilizer 74 can optionally also be constructed so as to be lengthwise or longitudinally positionally adjustable to accommodate a wide range of patients of different size. The knee stabilizer can also be side-to-side adjustable as well. Alternatively, the knee stabilizer 74 can be mounted in a fixed position relative to the table assembly 52, whereby the position of the patient on the table assembly 52 and relative to the knee stabilizer 74 may be adjustable. In either embodiment, the knee stabilizer 74 should be positioned or positionable to contact the knee or patella at the lower end of a patient's femur and thigh, as depicted in FIG. 5.

The knee stabilizer 74 acts as a knee or patellar clamp and can include a framework 76 arranged to surround and clamp onto a patient's joint or knee. The knee stabilizer 74 in this example has a pair of patellar clamping elements including an upper clamping element 78a and a lower clamping element 78b that are vertically spaced apart and adjustable relative to one another along the framework 76. The patellar clamping elements 78a, 78b can be vertically adjusted in order to clamp or otherwise securely hold the lower end of a patient's right femur and patella in a substantially fixed vertical position during testing, evaluation, or treatment, as described below. If the knee stabilizer 74 is positionally adjustable, it should be capable of being secured in a fixed selected position, once properly adjusted for a given patient, relative to the table assembly 52 and/or robot 54 during testing. The configuration and construction of the knee stabilizer 74 can vary considerably from the example shown herein. The patellar clamping elements 78a, 78b can be replaced by other suitable securing or clamping devices or elements and the mechanisms to adjust and secure the knee stabilizer 74 can also vary.

Though not shown in all of the figures, the knee stabilizer 74 can include a plurality of substantially rigid and/or resilient pads for holding and restraining the knee and patella of a patient. See FIGS. 3-6. In one example, the knee stabilizer knee can include a pair of side-to-side opposed Varus-valgus pads 75 that are adjustable, as shown and described below, toward and away from one another across the framework 76. The knee stabilizer 74 can also include one or more upper pads 77 on the upper clamping element 78a and a lower pad 79 on the lower clamping element 78b. The pads 75, 77, and/or 79 can be configured and arranged to lie adjacent the patient's knee. The various pads 75, 77, and 79 can be configured to prevent the framework 76 and the patellar clamping elements 78a, 78b from directly contacting the patient's knee, but also to assist in restraining the knee and inhibiting movement during testing. The pads 75, 77, and/or 79 can be solid, hollow, pressurized, hydraulically filled, pneumatically filled, or the like and can be rubber, foam, or otherwise formed of suitable materials. In one example as shown, the pad or pads 77 on the upper patellar clamping element 78a can be configured to define a V-shape within the framework 76. The patient's leg can then be captured within the V-shape as the upper and lower patellar clamping elements 78a, 78b are drawn toward one another to capture and hold the patient's leg still during a procedure. In particular, the stabilizer 74 and these pads 77 can aid in constraining the patella during testing. The Varus-valgus pads 75 can also be adjusted to restrain movement of the patient's knee in a side-to-side direction during at least Varus-valgus testing, as described below. In one example, the knee stabilizer 74 can also include a vertically displaceable patellar sensor 73, which can be mounted to the upper clamping element 78a, as depicted in FIGS. 3-6. Any residual movement in the knee and patella of a patient, when the stabilizer is clamped onto their knee, can be measured and accounted for, i.e., eliminated, in computing the data and analyzing the joint as described further below. The patellar sensor is disclosed and described in U.S. Application Ser. No. 62/258,191 filed Nov. 20, 2015 and entitled "Floating Patella Sensor, Patella Clamp with Floating Patella Sensor, and Robotic Knee Testing Device with Same." This prior filed application is hereby incorporated by reference herein in its entirety.

The thigh stabilizer 70 and/or the knee stabilizer 74 may be mechanically adjustable to manually fit and accommodate different sized patients. In one alternative, the thigh stabilizer 70 and/or the knee stabilizer 74 may be electrically operable to adjust the femur clamping elements 72, the patellar clamping elements 78a, 78b, respectively, or both. In another alternative example, the femur clamping elements 72 and/or the patellar clamping elements 78a, 78b may be pneumatically or hydraulically operable to adjust the thigh and knee stabilizers 70 and 74. In yet another alternative, the thigh stabilizer 70, the knee stabilizer 74, or both, may include two or more such systems or mechanisms for adjusting the respective clamping elements.

The thigh stabilizer 70 and/or femur clamping elements 72 and the knee stabilizer 74 and/or framework 76 and patellar clamping elements 78a, 78b can be formed of metal, plastic, or other suitable materials. The thigh and knee stabilizers 70 and 74 can vary in shape, configuration and construction, as desired. The thigh and knee stabilizers 70 and 74, in combination, are intended to secure a patient's leg in order to hold the femur and patella in a vertically (knee stabilizer) and laterally (thigh stabilizer) fixed position during a test, evaluation, or treatment cycle. Features and aspects of the disclosed thigh and knee stabilizers 70 and 74 can vary considerably while accomplishing this objective.

In this example as shown in FIGS. 2 and 4, the sub-frame 68 is configured to define or carry one or more slide tracks 80. The track or tracks 80 can be carried on the free end of the sub-frame 68 that is distal or spaced from the table assembly 52. The sub-frame 68 is formed having a plurality of rails 82 that extend lengthwise and having one or more cross-members 84 that extend laterally between the rails. The tracks 80 can be formed as an integrated part of the rails 82 or other sub-frame components or, as in this example, can be separately mounted to or supported by the rails and/or cross-members 84. One or more trucks or carriages, hereinafter a sled assembly 86 is mounted on or supported by the sub-frame 68 and is slidable along the tracks 80. The sled assembly 86 can slide along the tracks 80 to adjust the position of various parts of the RKT apparatus 50, as described further below. The sled assembly 86 can include a locking mechanism 88 (shown only in FIG. 2) to secure the sled assembly in a desired or selected position along the tracks 80. The locking mechanism 88 can vary in construction and position on the apparatus, as long as it can adequately secure the sled assembly at a selected position.

Adjustment of portions of the RKT apparatus 50 can be achieved in other ways. In one example, the RKT apparatus can be mounted to a lift that can raise or lower the apparatus, or portions thereof, and that can slide or roll the robotic components relative to the table assembly 52, either eliminating or altering the need for the tracks 80 and rails 82.

As depicted in FIGS. 2-4, the right leg portion 66 further includes a tibia positioning assembly 90 that is mounted on the sub-frame 68. In this example, the tibia positioning assembly 90, or at least a portion of the assembly, is carried on the sled assembly 86. Thus, the tibia positioning assembly 90, or at least a portion thereof, is slidable lengthwise along the tracks 80 of the sub-frame 68 on the sled assembly 86, and thus is movable relative to the table assembly 52 and/or to the thigh and knee stabilizers 70 and 74.

In general, the tibia positioning assembly 90 has a foot holder, which in one example can be a foot plate 92, as in this example. The foot plate 92 has a heel stop 93 at the bottom edge of the foot plate that faces upward and has a contact surface 94 that faces toward the thigh and knee stabilizers 70 and 74. The tibia positioning assembly 90 also has a tibia rod device 96 with one or more rods 98 and a calf contacting or loading portion, which in one example can be a calf plate 100 as in this example. The calf plate 100 is disposed at or near a distal end of the tibia rod device 96. The one or more rods 98 can be lengthwise adjustable. In this example as shown in FIGS. 2-4, the tibia rod device 96 has two tibia rods 98, each of which has two telescoping segments including a fixed segment 98a and a slidable segment 98b that permit length adjustment of the rods 98. Though not shown or described in detail herein, the rods 98 may include a locking mechanism of a suitable type, such as holes and set screws, VALCO ball devices, or the like on one or both of the segments 98a, 98b, that can lock the adjusted rods at a selected length. The telescoping segments permit adjustable positioning of the calf plate 100 relative to the foot plate 92 to accommodate different sized patients. During use, the calf plate 100 lies under and contacts a patient's calf below the knee and the foot plate 92 bears against the sole of the patient's foot. The foot plate 92 can be configured to physically constrain and hold the foot of a patient against the contact surface 94. In one example, though not shown herein, the foot plate 92 can employ one or more straps that secure the patient's heel against the heel stop 93 and the sole of their foot to the foot plate 92. Likewise, the calf plate 100 can be configured to physically constrain the patient's leg to the calf plate, as described below for certain tests, or can merely lie against and under the patient's calf while not being otherwise secured to the leg for other tests.

Figure 6:
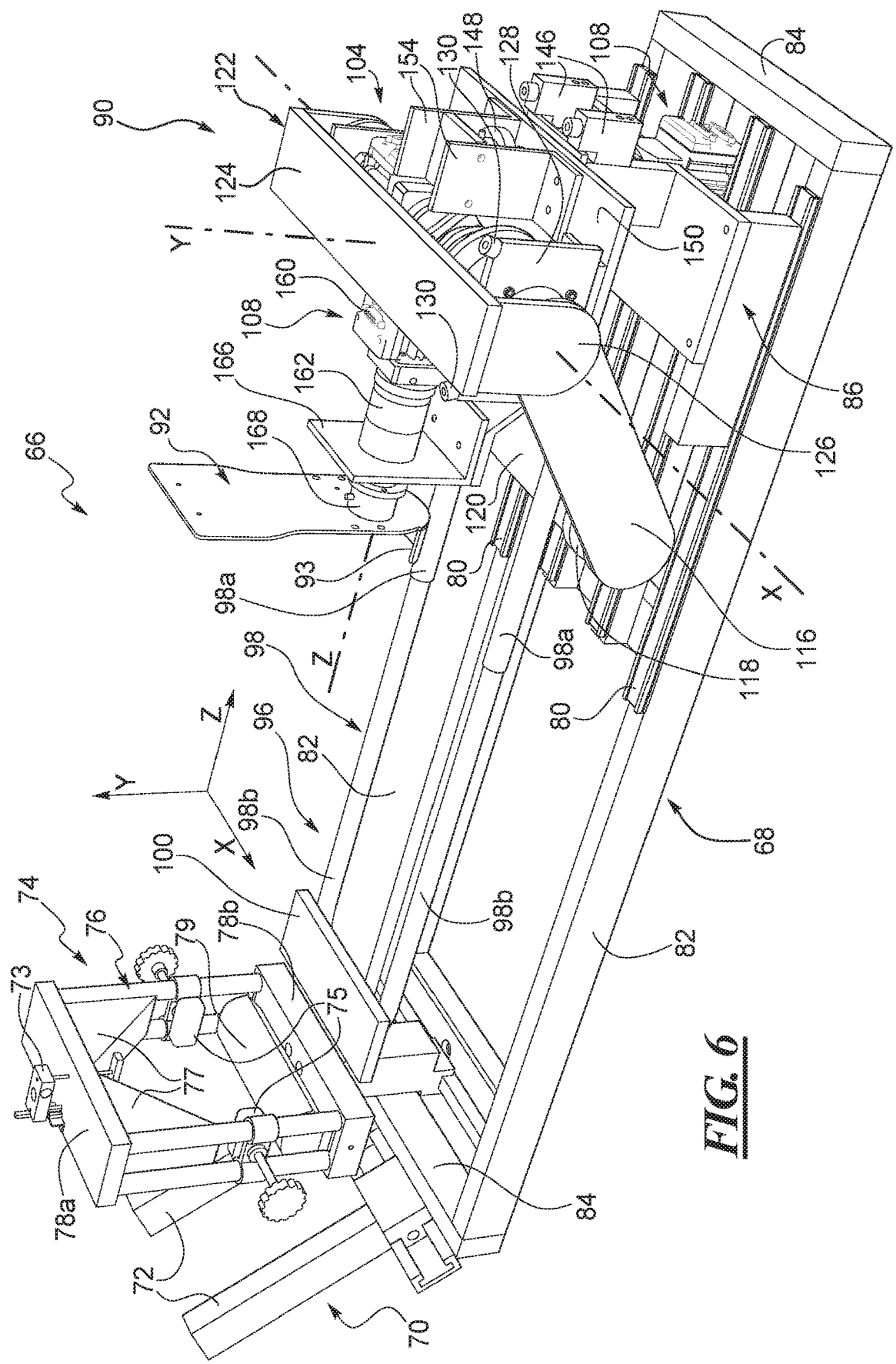
FIG. 6 shows the right leg portion of the robot of FIG. 2 and depicts an X-Y-Z coordinate system defined by the right leg portion.

With reference to FIGS. 4 and 6, the tibia positioning assembly 90 has a drive system with a number of drive components configured to impart specific and controllable movements to the lower leg of a patient. In this example, a substantial number of the drive system components are housed within a shell or housing 102. In other examples, the drive system components may be exposed and the shell eliminated. The drive system in this example generally has a first drive, i.e., an X-axis drive 104 as identified herein, which is oriented to define and provide rotation about a first axis, i.e., an X-axis as identified herein, which in this example lies generally laterally across the tibia positioning assembly 90. The drive system also has a second drive, i.e., a Y-axis drive 106 as identified herein, which is oriented to define and provide rotation about a second axis, i.e., a Y-axis as identified herein, which in this example lies generally vertically through the tibia positioning assembly 90, though not quite intersecting the X-axis, as described below. The drive system further has a third drive, i.e., a Z-axis drive 108 as identified herein, which is oriented to define and provide rotation about a third axis, i.e., a Z-axis as identified herein, which in this example lies lengthwise along the tibia positioning assembly 90. The three axes define a coordinate system and this coordinate system is identified as an X-Y-Z coordinate system for the right leg portion 66 of the robot 54 in this example. The robot will also have a similar X-Y-Z coordinate system specific to the left leg portion 64, but independent of the coordinate system for the right leg portion 66.

In other examples, the RKT apparatus may be configured to test only one or two of anterior-posterior motion, Varus-valgus motion, or tibial rotation, instead of all three tests. In such cases, the drive system may include only one or two of the X-axis, Y-axis, or Z-axis drives instead of all three drives. The methods and procedures described herein may be modified to accommodate such robots that have fewer than all three drives. In other examples, the X-Y-Z axes of the aforementioned coordinate systems may all intersect with one another and may all be orthogonal to one another. In still other examples, none or only two of the axes may intersect and/or none or only two of the axes may be orthogonal to one another.

As shown in FIG. 4, the X-axis drive 104 can include a first motor, such as an electric motor 110, a gearbox 112, and an output shaft 114 that is driven by the motor and gearbox. The opposite ends of the output shaft 114 in this example are fixedly coupled to the upper ends of respective drive links 116 on opposite sides of the housing 102. Thus, as the output shaft 114 is rotated by the motor 110 and gearbox 112, the drive links 116 are also rotated about the X-axis. The drive links 116 in this example are oriented downward and forward from the X-axis. The lower end of one of the drive links 116 is coupled or fixed to a rotational sensor or X-axis torque transducer 118. The torque transducer 118 can be of the type that would measure any movement, not just rotational movement, as well as the torque applied at the sensor. However, the torque transducer 118 is said to be a rotational sensor herein to distinguish it from other sensors mentioned below and because, during use, it may be primarily sensing torque and rotational movement, as compared to translational movement. The torque transducer 118 is also coupled or fixed to one end of a cross-plate 120. The lower end of the other drive link 116 is fixed to the opposite end of the drive plate 120. The cross-plate 120 is coupled to and extends laterally across the right leg portion 66 forward of the X-axis between the drive links 116. In this example, the fixed segments 98a of the tibia rods 98 are fixedly mounted to and extend forward toward the knee and thigh stabilizers 70, 74 from the cross-plate 120, as shown in FIGS. 2 and 4.

Figure 7:
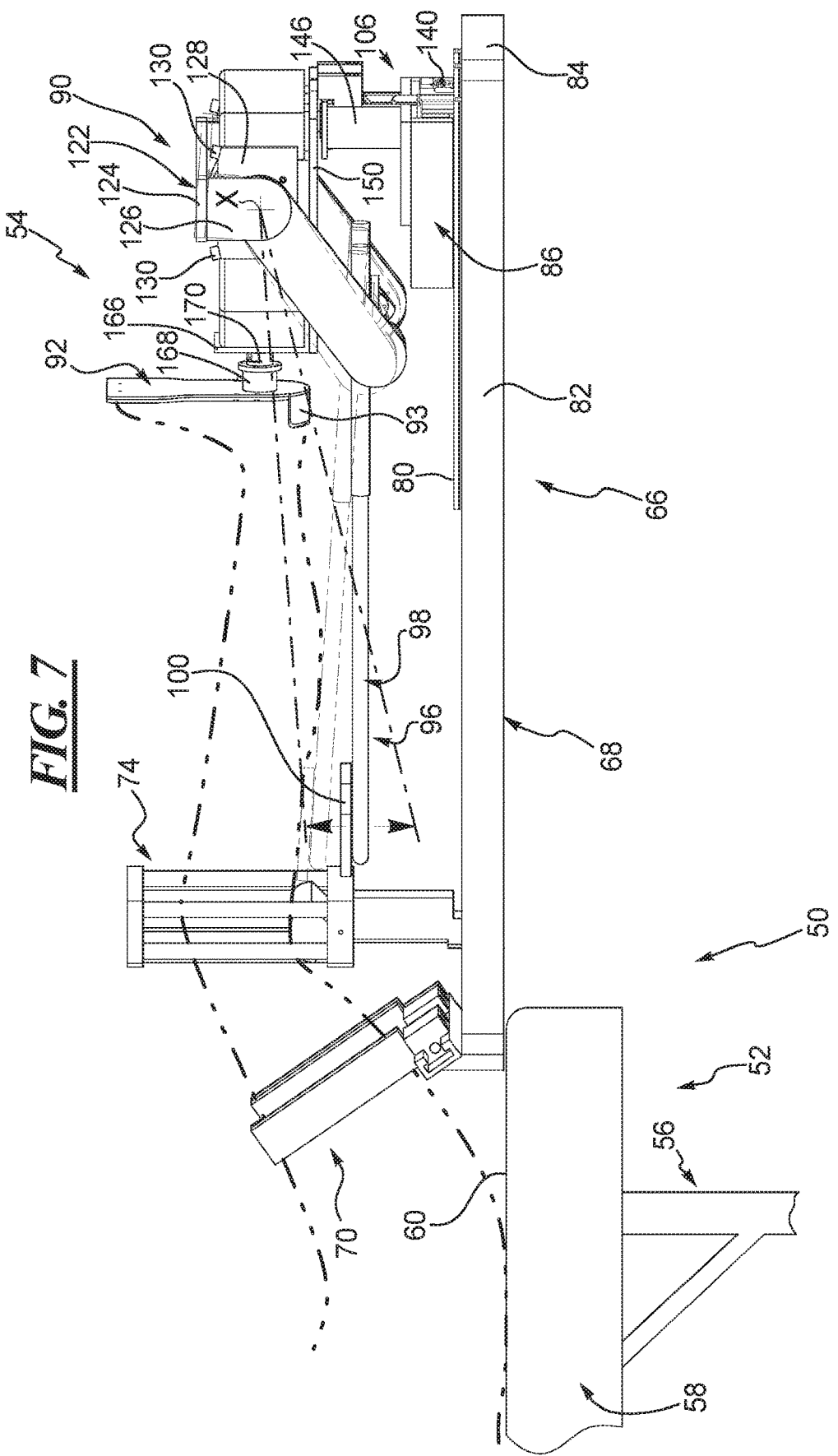
FIG. 7 shows a side view of the robot of FIG. 5 and illustrates anterior-posterior motion of the robot about the X-axis of the right leg portion of the robot.

With reference to FIG. 7, the X-axis drive 104 is configured to conduct an anterior-posterior or A-P test on a patient's knee. As noted below, translation or position sensors can be applied to appropriate locations on the right leg of the patient. The X-axis drive 104 imparts force about the X-axis to initiate anterior-posterior motion in the tibia part of the knee joint relative to the fixed femur part of the knee joint of the patient, as shown in FIG. 7. The motor 110 can reversibly rotate the output shaft 114 through an arc about the X-axis whereby the upper ends of the drive links 116 are rotated through the same arc. This in turn moves, i.e., raises or lowers the lower ends of the drive links 116, which in turn raises or lowers the cross-plate 120 and the fixed segments 98a of the tibia rods 98. Movement of the fixed segments 98a of the tibia rods 98 raises or lowers the slider segments 98b and thus the calf plate 100 carried on the tibia rods 98.

The X-axis torque transducer 118 measures the degree of rotation and applied torque at the cross-plate 120 caused by the load applied at the calf plate 100 as the calf plate pushes up on the patient's tibia or the tibia rods 98 pull down on the patient's tibia. Rotation, translation, and load data can be collected by a processor from the sensors relative to the motion in the patient's leg and from the X-axis torque transducer 118 relative to the torque or applied force.

The motor 110 and/or gearbox 112 can be designed to produce a limited range of travel, which may be substantially less than 360 degrees of rotations, in the output shaft 114. In addition or in the alternative, the X-axis drive 104 can also be designed to incorporate a mechanical travel limiter, if desired. In one example as shown in FIGS. 3, 4, 6, and 7, a yolk assembly 122 can be provided as part of the X-axis drive 104. The yolk assembly 122 has a top plate 124 extending over a top of the housing 102. The yolk assembly 122 also has a pair of side plates 126 extending down from the top plate 124. The side plates 126 can be affixed to the upper ends of the drive links or otherwise to the drive shaft 114 of the motor 110, so that the yolk assembly 122 also rotates with the drive shaft. A stop bracket 128 is disposed at one end of the motor 110 adjacent one of the yolk side plates 126. Two stops 130, i.e., fore and aft travel stops protrude upward from the stop bracket 128. The stops 130 are positioned and circumferentially spaced apart relative to the X-axis. The top plate 124 of the yoke assembly 122 is captured between the two stops and hits one of the stops to limit travel of the yoke assembly in either rotation direction. The radius of the side plates 126 and spacing of the stops 130 can thus limit rotational travel of the output shaft 114 to a specific arc, which mechanically limits the upward and downward travel of the tibia rods 98.

The above-described anterior-posterior movement components of the tibia positioning assembly 90 can vary considerably from the example shown and described herein. The yoke assembly 122 and stop bracket 128 can be eliminated or can take on different positions, configurations, and constructions. Instead, another mechanical stop mechanisms can be employed. Likewise, the configuration and construction of the drive links 116, cross-plate 120, tibia rods 98, and calf plate 100 can also be varied. The mechanisms or devices that are used to secure a patient's leg to the tibia rods 98 and to the foot plate 92, if and when needed for testing, can also vary.

As shown in FIGS. 4 and 6, the Y-axis drive 106 can include a second motor, which can also be an electric motor 140, a gearbox 142, and an output shaft 144 that is driven by the motor and gearbox. The gearbox 142 and motor 140 are fixed to the sled assembly 86 beneath the X-axis drive 104. Thus, the entire tibia positioning assembly 90, including the Y-axis drive components, can slide lengthwise along the sub-frame 68 to adjust the foot plate 92 position relative to the table assembly 52 and/or the thigh and knee stabilizers 70, 74. The motor 142 can be secured to a motor mount or bracket 146 that is carried on the sled assembly 86. A Y-axis rotation sensor or torque transducer 148 is fixed to the output shaft 144 for rotation therewith. The torque transducer 148 can also be of the type that measures any movement, not just rotational movement, as well as the torque applied at the sensor. However, the torque transducer 148 is said to be a rotational sensor herein to distinguish it from other sensors mentioned below and because, during use, it may be primarily sensing torque and rotational movement, as compared to translational movement. A pivot plate 150 can be sandwiched between a pair of thrust bearings 152 with the Y-axis drive below the pivot plate and the Y-axis torque transducer above the pivot plate. Support brackets 154 are secured to the top of the pivot plate 150 and the torque transducer 148 is fixed to the support brackets. The pivot plate 150 is disposed on top of the motor mounts 146 in this example and can rotate relative to the mounts and the sled assembly 86. The shell 102 can be secured to the pivot plate 150 to create an enclosure for the X-axis drive 104 and the Z-axis drive 108. Thus, as the output shaft 144 is reversibly rotated by the motor 140 and gearbox 142 about the Y-axis, as represented in FIG. 8, the shell 102, pivot plate 150, X-axis drive 104, Z-axis drive 108, foot plate 92, and tibia rods 98 will all rotate about the Y-axis.

Figure 8:
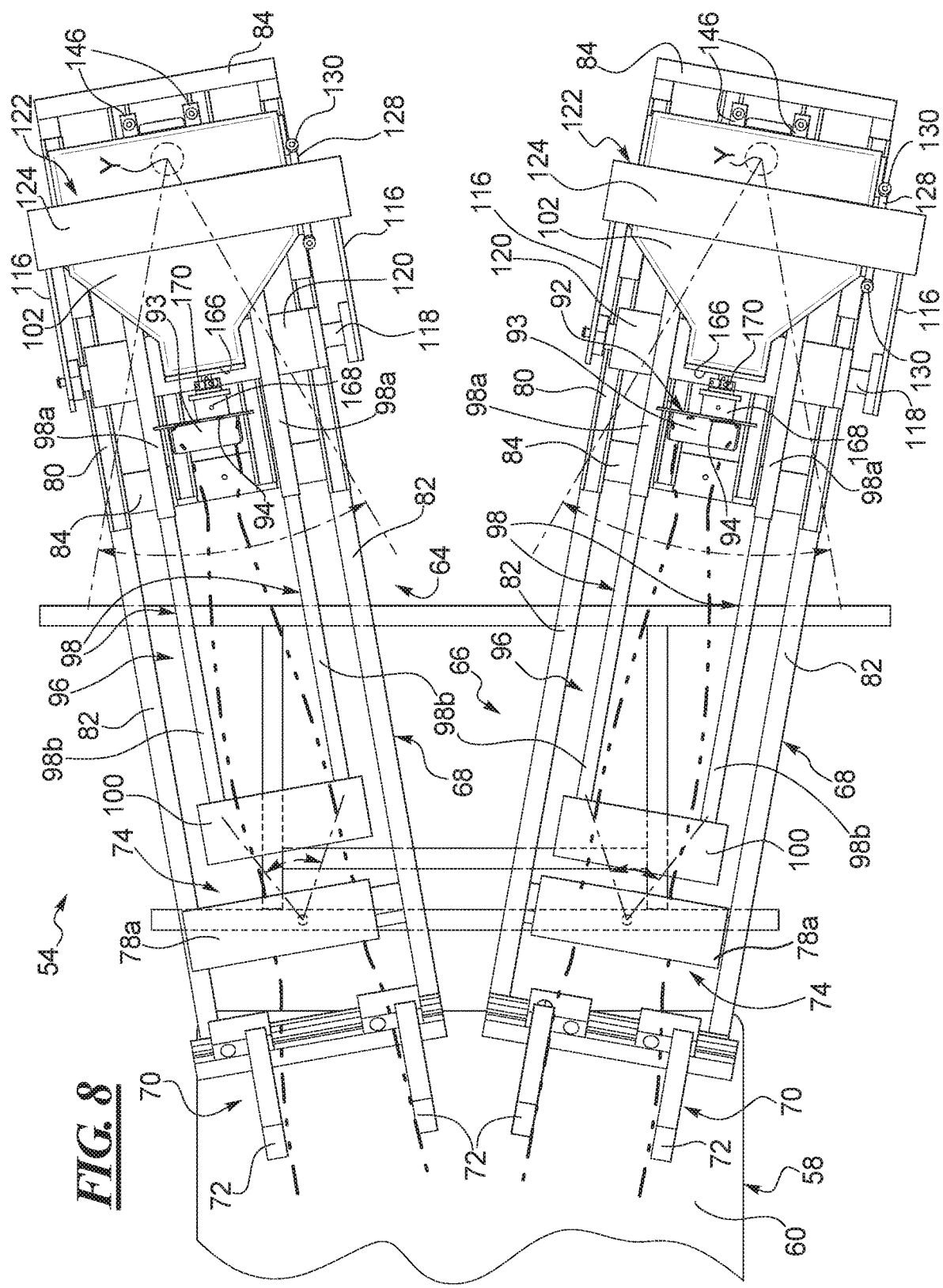
FIG. 8 shows a top view of the robot of FIG. 5 and illustrates Varus-valgus motion of the robot about the Y-axis of each of the left and right leg portions of the robot.

As represented in FIG. 8, the Y-axis drive 106 is configured to conduct a Varus-valgus or V-V test on a patient's knee. As described below, translation or position sensors can be applied to appropriate locations on the right leg of the patient. The Y-axis drive 106 imparts force about the Y-axis to initiate Varus-valgus motion in the tibia part of the knee joint relative to the fixed femur part of the knee joint of the patient, as shown in FIG. 8. The motor 140 can reversibly rotate the output shaft 144 through an arc about the Y-axis whereby the pivot plate 150 is rotated through the same arc. This in turn moves, i.e., pivots the Z-axis drive 108 side-to-side, which in turn pivots the foot plate 92 and the tibia rods 98 about the Y-axis. Movement of the tibia rods 98 moves the patient's lower leg side-to-side relative to the femur. The Y-axis torque transducer 148 measures the degree of rotation and applied torque at the output shaft 144 caused by the load applied at the calf plate 100 or along the tibia rods as the tibia rods push the patient's tibia medially or laterally relative to the femur. Rotation, translation, and load data can be collected by a processor from the sensors relative to the motion in the patient's leg and from the Y-axis torque transducer 148 relative to the torque or applied forces.

The motor 140 and/or gearbox 142 can be designed to produce a limited range of travel, which may be substantially less than 360 degrees of rotations, in the output shaft 114. In addition or in the alternative, the Y-axis drive 108 components can also be designed to incorporate a mechanical travel limiter, if desired, though not shown or described herein.

The above-described Varus-valgus movement components of the tibia positioning assembly 90 can also vary considerably from the example shown and described herein. The sled assembly 86, motor mounts 146, pivot plate 150, and support brackets 154 can be eliminated or can take on different positions, configurations, and constructions. For example, the pivot plate 150 can include a curved guide slot 156 formed through the plate, as shown in FIG. 4. The guide slot 156 can be spaced a radial distance from the Y-axis and the output shaft 144 of the motor 140. A guide post 158 can be fixed to the sled assembly 86 and project upward toward the guide slot 156. A tip 159 of the guide post 158 can be captured in or seated in the guide slot and can be configured to both support the pivot plate 150 thereat and to slide along the guide slot as the pivot plate is rotated by the motor 140. Likewise, the configuration and construction of the cross-plate 120, tibia rods 98, calf plate 100, shell 102, and the like can also be varied. The mechanisms or devices that are used to secure a patient's leg to the tibia rods 98 and to the foot plate 92, if and when needed for testing, can also vary.

As shown in FIGS. 4 and 6, the Z-axis drive 108 can include a third motor, which can also be an electric motor 160, a gearbox 162, and an output shaft 144 that is driven by the motor and gearbox. The gearbox 162 and motor 160 are fixed to a motor mounting bracket 166 that is attached to a front end of the pivot plate 150 and forward of the X-axis drive 104. In this example, the Z-axis is aligned with both the X-axis and the Y-axis, though in other examples this might not be the case. The entire Z-axis drive, including the foot plate 92, can also slide lengthwise along the sub-frame 68 to adjust the foot plate 92 position relative to the table assembly 52 and/or the thigh and knee stabilizers 70, 74 as noted above. A Z-axis rotation sensor or torque transducer 168 is fixed to the output shaft 164 by an adaptor 170 for rotation therewith. The torque transducer 168 can be of the type that would measure any movement, not just rotational movement, as well as the torque applied at the sensor. However, the torque transducer 168 is said to be a rotational sensor herein to distinguish it from other sensors mentioned below and because, during use, it may be primarily sensing torque and rotational movement, as compared to translational movement. In this example, the motor 160 and gearbox 162 are positioned behind the motor mounting bracket 166 and the adaptor 170 and torque transducer 168 are disposed forward of the mounting bracket. The enclosure defined by the shell 102 and the pivot plate 150 house the Z-axis drive 108, other than the foot plate 92, as noted above. The foot plate 92 is secured to the torque transducer 168 for rotation therewith. Thus, as the output shaft 164 is reversibly rotated by the motor 160 and gearbox 162 about the Z-axis, as shown in FIG. 9, the foot plate 92 will all rotate about the Z-axis.

Figure 9:
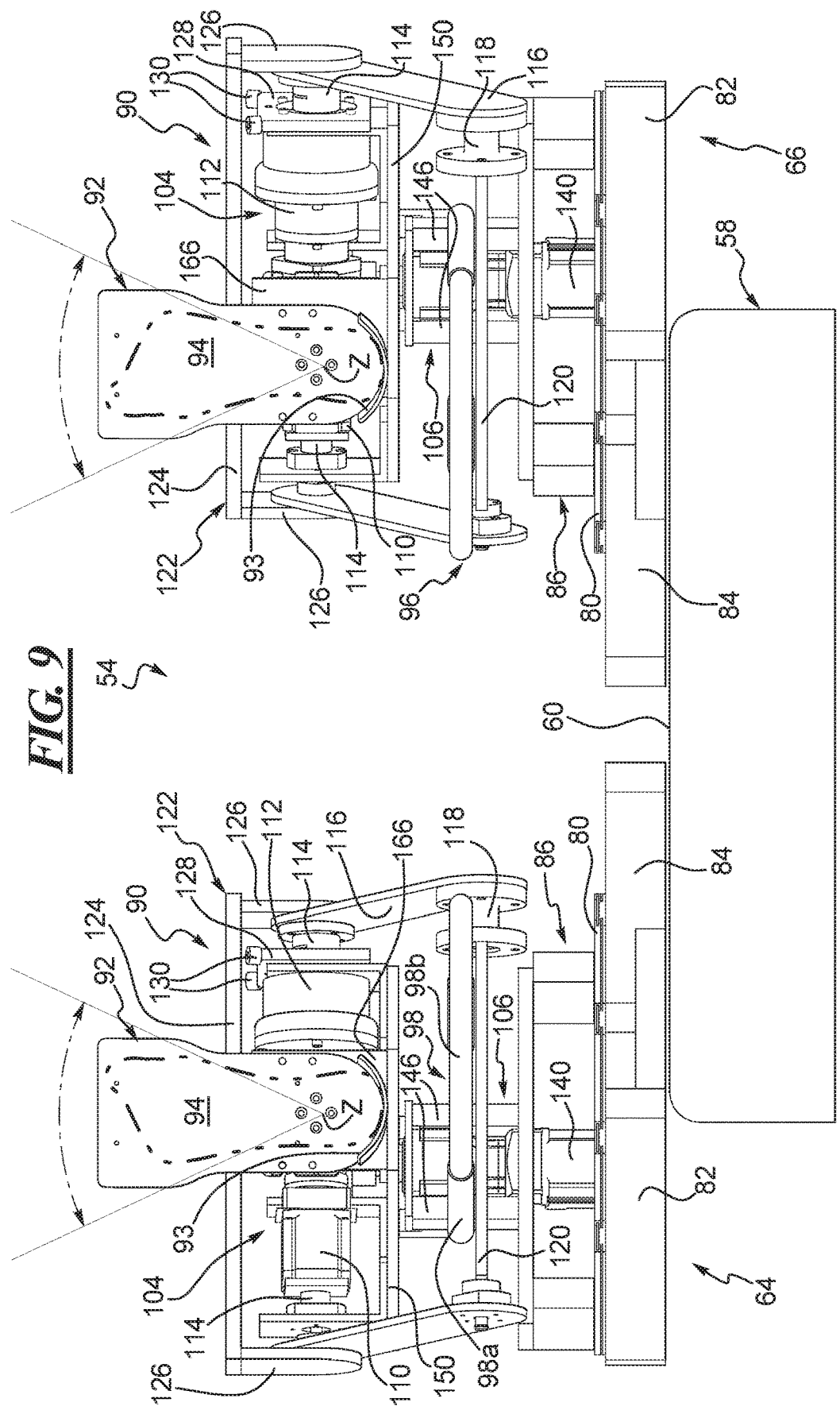
FIG. 9 shows an end view of the robot of FIG. 5 from the point of view and in the direction of the arrow IX and illustrates internal and external rotation of the robot about the Z-axis of each of the left and right leg portions of the robot.

As represented in FIG. 9, the Z-axis drive 108 is configured to conduct an internal and external rotation or simply a tibia rotation test on a patient's knee. As described below, translation or position sensors can be applied to appropriate locations on the right leg of the patient. The Z-axis drive 108 imparts force about the Z-axis to initiate rotation motion in the tibia part of the knee joint relative to the fixed femur part of the knee joint of the patient, as shown in FIG. 9. The motor 160 can reversibly rotate the output shaft 164 through an arc about the Z-axis whereby the adapter 170 and torque transducer 168 are rotated through the same arc. This in turn moves, i.e., rotates the foot plate 92 about the Z-axis. Movement of the foot plate 92 in this manner rotates the patient's lower leg internally and externally relative to the femur. The Z-axis torque transducer 168 measures the applied torque at the output shaft 164 caused by the load applied at the foot plate 92 as the foot plate rotates the patient's tibia or lower leg internally and externally relative to the femur. Rotation, translation, and load data can be collected by a processor from the sensors relative to the motion in the patient's leg and from the Z-axis torque transducer 168 relative to the torque or applied forces.

The motor 160 and/or gearbox 162 can be designed to produce a limited range of travel, which may be substantially less than 360 degrees of rotations, in the output shaft 164. In addition or in the alternative, the Z-axis drive 108 components can also be designed to incorporate a mechanical travel limiter, if desired. A simple mechanical stop can be positioned to stop movement of the foot plate 92 in either rotation direction, if desired. Such a sop can be the tibia rods 98 or something mounted thereto. Alternatively, such a stop can be applied to the motor mounting bracket 166 or the like.

The above-described rotation movement components of the tibia positioning assembly 90 can also vary considerably from the example shown and described herein. The foot plate 92 and motor mounting bracket 166 can be eliminated or can take on different positions, configurations, and constructions. The mechanisms or devices that are used to secure a patient's leg to the foot plate 92, if and when needed for testing, can also vary.

The above described motors, gearboxes, and output shafts can also vary within the scope of the disclosure. The motors can be servo-motors or other types of motors suitable for precise motion and torque control and for the loads to which the motors will be exposed during such limb testing and evaluation. Any of the first, second, or third, i.e., the X-, Y-, or Z-axis drives with respect to the motors and gearboxes can be structurally configured substantially the same relative to one another, with the only substantive difference being the relative axis of rotation about which each is oriented. Alternatively, each drive can incorporate a motor and/or gearbox that is different than one or both of the others as well. The torque transducers can be selected in order to provide torque readings as known in the art relating to each of the three drives. In other examples, one or more of the torque transducers may be replaced with other torque or load sensors or load sensing means. For example, motor current may be measured to determine the torque or load on the motor output shaft during use. Any suitable means for modeling torque may be used. The torque readings can be calibrated and calculated as needed to correspond to known torque or force values imparted to a patient's limb(s). Movement of the patient's body parts may be detected by non-invasive systems, as noted above, that utilize sensors or markers that are attached to the skin, including but not limited to vision, optoelectronic, ultrasonic, and electromagnetic motion analysis systems.

In use, a patient lies on the padded surface 60 of the platform 58 on the table assembly 52 as shown in FIG. 5. The patient's knees are positioned to engage the knee stabilizers 74, their thighs are positioned to engage the thigh stabilizers 70, their feet are positioned to engage the foot plates 92, and their calves are positioned to engage the tibia rods. The patient can then be secured to the foot plates, to the knee stabilizers, and to the thigh stabilizers for testing and evaluation. The patient's calves or tibias can also be secured to the tibia rods 98, as needed for specific testing. Movement of the lower leg of the patient may be detected by non-invasive systems utilizing sensors or markers that are attached to the skin, including but not limited to optoelectronic, ultrasonic, and electromagnetic motion analysis systems. In one example, the RKT apparatus can be configured so that the patient's knees are flexed to about 30 degrees between the femur and the tibia. However, the tests or evaluations may also include the additional capability to flex the knee from 0 to 90 degrees to allow for similar tests (such as the examples above) done for different degrees of knee flexion. Though not disclosed in detail herein, the RKT apparatus can be configured to permit adjustment of one or more of the table assembly height, the tibia positioning assembly height, and/or, the relative horizontal positioning between the two in order to adjust patient knee flexion to a desired angle for testing.

Any one of the X-, Y-, and Z-drives can be decoupled from any of the other two. In the disclosed example, each of the three drive assemblies may be operable with one or more of the other at the same time or can be decoupled from each of the other two and be operable independent of the other two. In other examples, two or more, and perhaps all three of the drives can be mutually coupled relative to one another such that movements are substantially simultaneously imposed upon the patient's legs during use of the RKT apparatus. The combined simultaneous operation of two or all three of the motors allows the RKT apparatus to perform more complex testing, such as simulating the known manual pivot shift testing procedure.

One or more of the aforementioned sensors can be provided on the legs of a patient, in the power lines of the RKT apparatus, and/or on the X-, Y-, and Z-drives to obtain desired position or location data as the lower leg is moved during testing and evaluation. The degree of movement of the patient's legs in the A-P test, the V-V test, and/or the rotation test can be measured by detecting the movements of the parts of the apparatus, the rotation of the drives, and/or the actual movements of the patient's legs. The torque encountered during each test and over the range of motion applied during each such movement may also be measured, suitably calibrated to the limb movement, and recorded. Various X-, Y-, and Z-axes can also be determined and recorded, as described below, for and/or relating to the femoral and tibial axis of the patient for testing.

The robot testing apparatus 202 is configured to implement rotational joint testing and translational joint testing of a joint. The robot testing apparatus 202 implements the rotational and translational joint testing to acquire or capture rotational and translational data indicative of rotational and translational movement of the joint during the rotational and translational joint testing, respectively. For instance, in implementing such testing, the robot testing apparatus 202 may be configured to detect a range of rotational motion and a range of translational motion for the joint. Other types of data indicative of rotational and translational movement of the joint during the rotational and translational joint testing may be acquired. For instance, the rotational and translational data acquired by the robot testing apparatus 202 may be indicative of a position (e.g., a relative position) of the joint for a given torque level.

Various types of rotational and translational joint testing may be implemented by the RKT apparatus 50. Other similar apparatuses may be developed to test other joints. In the disclosed example in which the joint is a knee, the rotational movement may be or include external-internal rotational movement and/or Varus-valgus rotational movement. The translational movement may be or include anterior-posterior movement. Additional and/or alternative rotational and/or translational movements may be measured. The number of different rotational and translational joint tests implemented by the RKT apparatus 50 may vary accordingly.

As noted above, even testing and evaluation of knee joints using the RKT apparatus 50 can be inconsistent from patient to patient, from doctor to doctor, and from test procedure to test procedure by the same doctors and/or on the same patients. Such inconsistency is created at least in part because each stage or step of the set-up and testing procedures can introduce error into the process. The cumulative error can become quite substantial and thus significantly affect the accuracy of the test results. As disclosed herein, important stages or steps for each test are patient set-up and robot set-up. According to the teachings of the present disclosure, providing a consistent method or procedure to set-up a patient relative to the RKT apparatus 50 has been determined to aid in producing more consistent test results and reducing error in the diagnosis and data. Further, according to the teachings of the present disclosure, providing a consistent method or procedure to set up or initialize the robot 54 of the RKT apparatus 50 prior to testing a given patient has also been determined to aid in producing more consistent test results and reducing error in the data. Also according to the teachings of the present disclosure, defining and utilizing a number of machine and/or anatomic criteria for each machine and/or patient have been determined to further aid in obtaining or producing more accurate and consistent test results.

Figure 10:
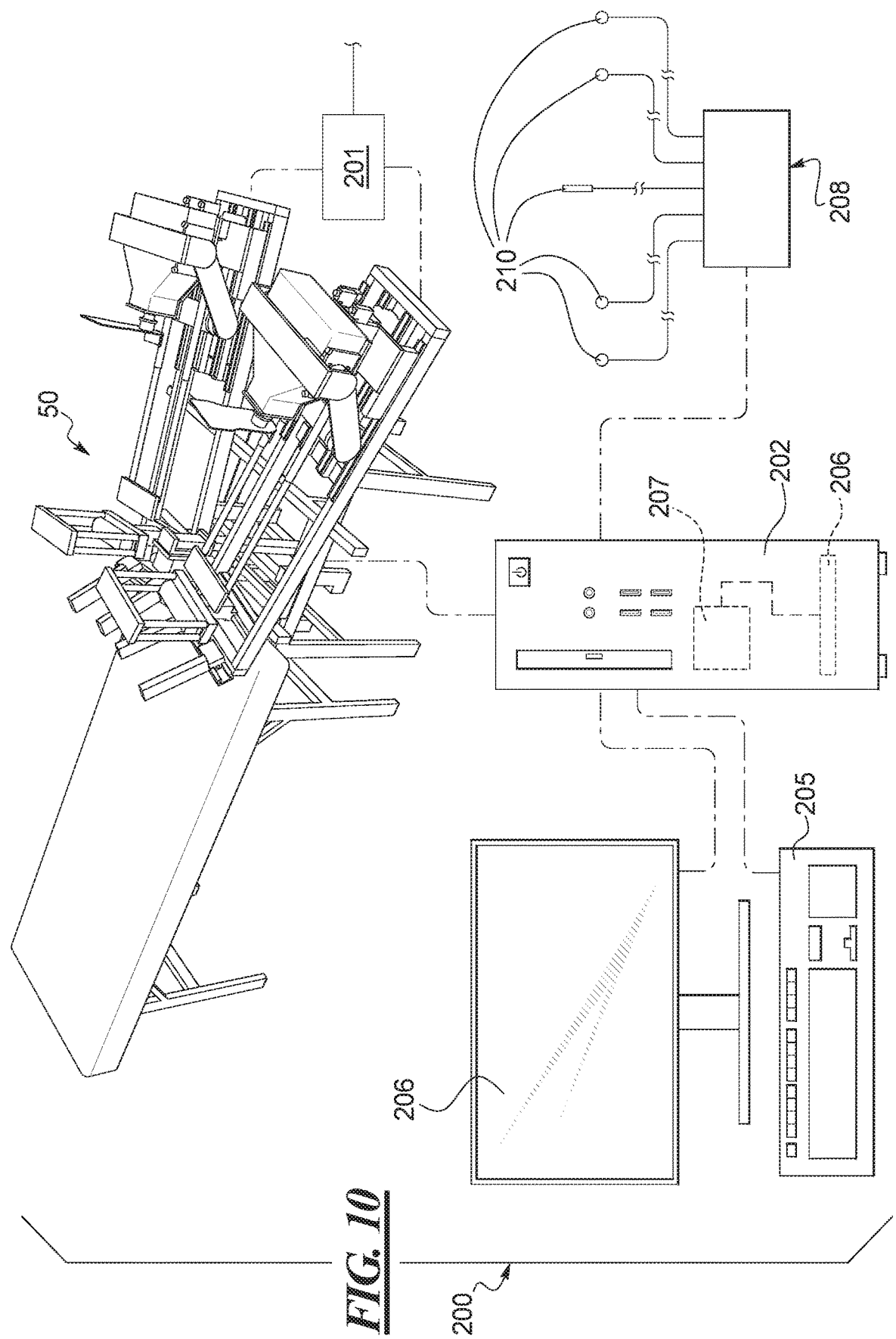
FIG. 10 shows an analysis system utilizing the RKT apparatus and robot of FIG. 1.

As shown in FIG. 10, the RKT apparatus 50 can be a part of or coupled to an analysis system 200. The robot 54 of the RKT apparatus 50 can be connected to a power source 201 to operate the robot. The power source 201 can be a typical 120/220 volt AC grid, a converted direct current power source, a stand-alone power source such as a generator or battery, or the like. The robot 54 of the RKT apparatus 50 can also be connected to a programmable electronic device or network of devices, such as a computer 202 or a computer network, a network server, or the like of the system 200. In any case, the computer 202 can have or be connected with an input device 204, such as a keyboard, a user display 205, such as a monitor or screen, a memory 206, and a processor 207. The robot 54 and/or computer 202 can also be coupled to a sensor or tracking system 208. The tracking system 208 can utilize one or more individual translation sensors 210 that are configured to detect or determine spatial positioning or location of the sensor at a point in time. One of the sensors can be provided on a pointer 212 that is freely movable to locate specific points while using the system 200, as described below. The sensors 210 and pointer 212 are coupled to a transmitter 214 of the tracking system 208. The earlier described rotational sensors or torque transducers 118, 148, 168 can also be coupled to the transmitter 214 to track their position in space as needed. The translation sensors 210 and associate with the pointer 212 can also be of the type that would measure any movement, not just translational movement. However, the translational sensors 210 and the sensor associated with the pointer 212 are said to be translational sensors herein merely to distinguish them from other sensors. All of the sensors mentioned herein may certainly be capable of sensing rotation about and translation along an axis as well as complex rotation and translation in space.

The types of sensors 210 and tracking system 208 can vary and in one example employ electromagnetic (EM) sensors, electromagnetic field (EMF) sensors, or other suitable sensor technology. The tracking system 208 can be utilized to determine the aforementioned X-, Y-, and Z-axes, and also described in more detail below, for the femoral and tibial axes of the patient prior to testing, either through placement of the sensors 210 on the patient's legs and/or by picking certain anatomic points on the user legs or specific points on the RKT apparatus, such as on the knee stabilizers, using the pointer 212.

The analysis system 200 includes a number of motors 110, 140, 160, one or more transducers or rotations sensors 118, 148, 168, one or more translational sensors 210, and a position sensor on as part of a pointer 212, each directed to capturing data for the rotational joint testing ("rotational sensors") and directed to capturing data for the translational joint testing ("translational sensors"). Each sensor is configured to capture data indicative of position as the rotational and translational joint testing is implemented. The motors 110, 140, 160, the rotational transducers or sensor(s) 118, 148, 168, the translational sensor(s) 210, and the position sensor or pointer 212 may be configured differently from the example as described above in connection with FIGS. 1-9. Also, each motor 110, 140, 160 may include a separate torque transducer to capture data indicative of the torque level applied to the joint and rotation sensor to capture the degree of rotation applied to the joint during the rotational and translational joint testing.

Figure 11:
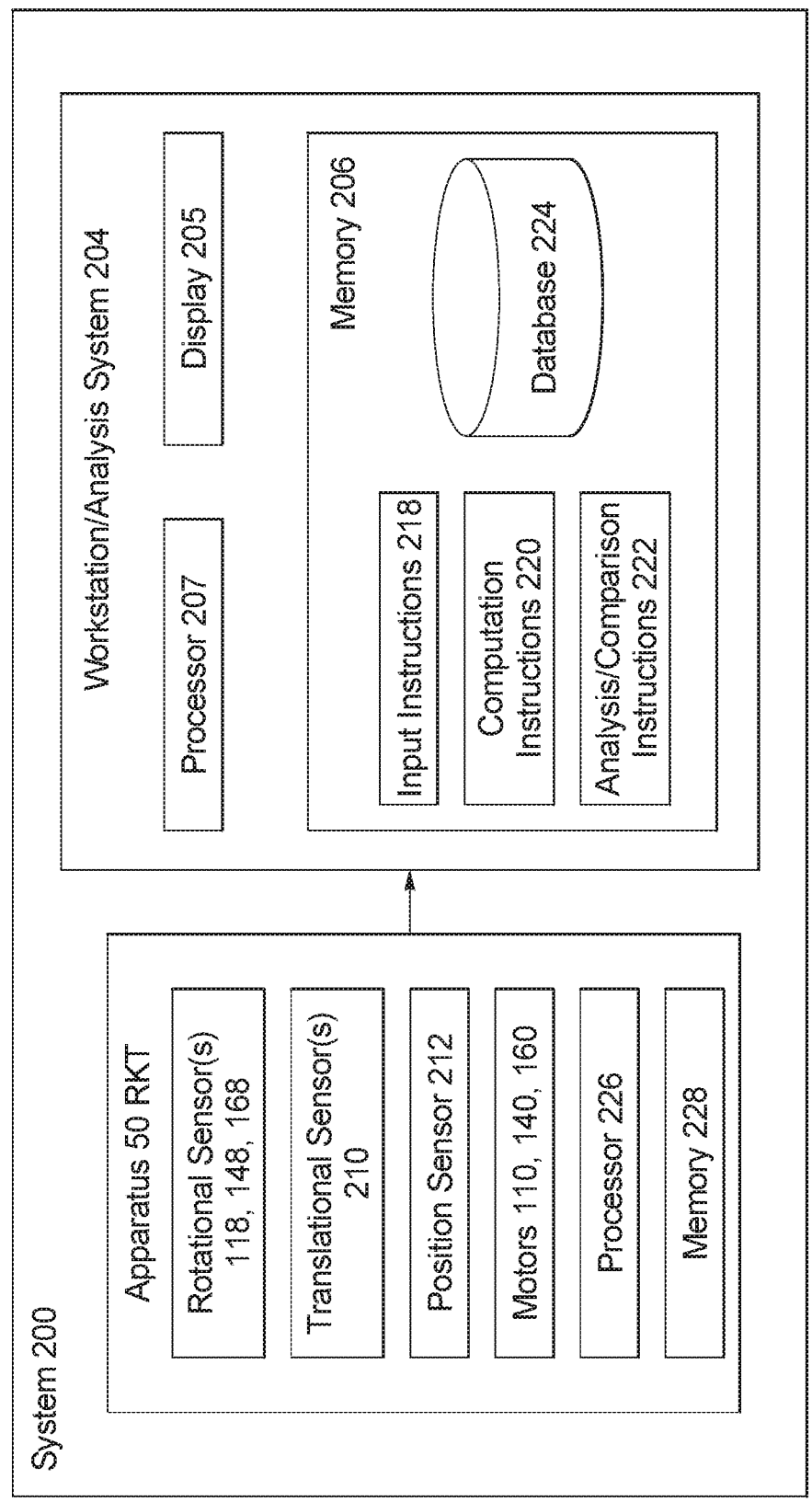
FIG. 11 shows a schematic illustration of the analysis system depicted in FIG. 10.

As represented in FIG. 11, the analysis system 200 includes the processor 207 and the memory 206 for processing the data captured by the RKT apparatus 50. The processor 207 is coupled to, or otherwise in communication with, the robot 54. In this example, the analysis system 200 also includes the display 216 that provides the user interface for an operator of the analysis system 200. The user interface may be directed to controlling the RKT apparatus 50, robot 54, and/or the analysis system 200. The user interface may be alternatively or additionally directed to presenting the results of the processing and testing.

The processor 207 is coupled to the memory 206 to access instructions and/or other data stored on the memory 206. In the example of FIG. 11, input instructions 218, computation instructions 220, and analysis instructions 222 are stored on the memory 206. The instructions 218, 220, 222 may be stored as one or more modules or instruction sets, and may be integrated to any desired extent. The memory 206 may have additional data stored thereon. The memory 206 may be or include any number of storage devices, memories, and/or other computer-readable media.

In the disclosed example, the X-, Y-, and Z-drives can be connected to and operable by the computer 202. The computer 202, including the memory 206 and processor 207, can be programmed or configured to receive and store load or torque data from the X-, Y-, and Z-drives 104, 106, 108, i.e., the rotation sensors or torque transducers 118, 148, 168, to receive and store rotation position data from the rotation sensors or torque transducers, and to receive and store spatial position data from the translation sensors 210 and pointer 212 of the tracking system 208. The processor 207 can be programmed or configured to perform calculations and to provide information, data, or feedback related to knee laxity, based on the data. The information, data, or feedback can be provided to the examiner on the display 205. The knee laxity information, data, or feedback can relate to anterior-posterior movement, Varus-valgus movement, and/or tibia rotation movement, as described above. Such knee laxity information, data, or feedback can also be used to provide a likely diagnosis of the injury to the knee.

As represented in FIG. 12, the set-up of the patient relative to the RKT apparatus 50 and particularly the robot 54 can be performed or specified as disclosed herein to aid in rendering the test data, information, and feedback more consistent and more accurate. Likewise, also as shown in FIG. 12, the set-up of the robot 54 prior to undertaking any testing can also be performed or specified to aid in rendering the test data, information, and feedback more consistent and accurate.

The methods and procedures disclosed and described below have been developed in an effort to make the patient set-up, apparatus or robot set-up, and initial conditions as repeatable and consistent as possible. FIG. 13 shows a block diagram that is representative of a set-up method according to the teachings of the present disclosure. In this example, the method combines steps relating to setting up the patient relative to the RKT apparatus and setting up the robot 54 prior to testing. In other examples, the method may include only steps to set-up the patient relative to the RKT apparatus 50 and robot 54. Likewise, the method may include only steps to set up the robot 54 prior to testing. Also in general, one can work from the head of the patient toward the toes of the patient during the set-up procedure. This can help to maintain consistency during set-up. Also, one can adjust one element on one side and then adjust the same element on the other side at each step before moving to the next adjustment.

With reference to FIG. 13, at block 300, the RKT apparatus 50 is turned on or powered up with power supplied by the power source 201. In the disclosed example, to do so, the computer 202 including the applicable program, the tracking system 208 including the sensors 210, 212, and the robot 54, including the motors 110, 140, 160 and sensors or torque transducers 118, 148, 168, are each started, turned on, or powered up. The objective of this step is to get the analysis system 200 including the RKT apparatus 50 up and running and to prepare the apparatus for use. Prior to or just after this step, the thigh stabilizers 70 and knee stabilizers 74 can be loosened or released to allow for positioning of the patient.

At block 302, the drives or motors of the robot 54 are leveled. In the disclosed example, to do so, the motors 110, 140, 160 of the corresponding X-, Y-, and Z-drives 104, 106, 108 can be precisely leveled relative to a horizontal or vertical reference or referencing a leveling device. In one example, a portion of the tracking system 208 can be used to precisely level the motors 110, 140, 160. Alternatively, the motors 110, 140, 160 can be leveled manually or mechanically such as by using an inclinometer or an optical encoder. The objective of this step is to provide and define a consistent, repeatable starting point for the tibia positioning assemblies 90 that can be achieved prior to each test using the RKT apparatus 50.

At block 304, the torque in each of the drives or motors is zeroed. In the disclosed example, to do so, each of the motors 110, 140, 160 of the drives 104, 106, 108 is zeroed with no torque or load on the motors. The motors 110, 140, 160 may thus be adjusted or re-set to a condition where the torque transducers 118, 148, 168 read zero torque when the output shafts are under no torque. The objective of this step is to provide and define a consistent and repeatable starting condition or base line, i.e., a baseline or zero torque starting point for each drive or motor prior to each test using the RKT apparatus 50.

At block 306, the patient is positioned or placed on or in the RKT apparatus 50 with their legs in position relative to the robot 54. In the disclosed example, to do so, the patient climbs onto or is positioned on the padded surface 60 of the platform 58 on the table assembly 52. The patient is then positioned with their legs adjacent the tibia positioning assemblies 90. First, the upper clamping elements 78a of the knee stabilizers 74 are removed so as to permit the legs of the patient to drop down onto the lower clamping element 78b (see also below at block 340). The patient and the patient's legs are then positioned so that the posterior joint line of each knee is directly over the front plane, i.e., the foot facing side of the corresponding knee stabilizer 74. One objective for this step is to provide a consistent, repeatable target position in the Z-axis direction for the knees of a patient with respect to the thigh and knee stabilizers 70, 74. A further objective is to set up the femoral epicondylar axis in a consistent manner for the left and right knees. In this position, the lower legs of a patient are also free to bend at the knee forward of the lower clamping elements 78b while the lower femur of each leg is fully supported on the pad 79 of the lower knee clamping element.

At block 308, the abduction angle of the patient's femurs is adjusted relative to their hips. In other words, the patient is positioned on the table assembly 52 and/or the tibia positioning assemblies 90 are adjusted so that their femurs are at a desired abduction angle. In one example, the tibia positioning assemblies 90 may each be pivotable about their respective proximal ends relative to the sub-frame 68 to allow angular adjustment of the assemblies, as depicted in FIG. 8. In one example, the angle and/or distance between the two assemblies 90 may be adjustable so that they are equivalent to ensure consistent set-up for both the left and right assemblies 90. The tibia positioning assemblies 90 may be pivotable or movable as depicted in FIG. 8 in order to adjust or change the angle between the two assemblies relative to a mid-line of the apparatus and/or the patient. This adjustment can be done in order to set up the abduction angle of the patient's femurs so that their femurs are neutrally aligned with their hips. The tibia positioning assemblies 90 may be adjustable to a desired abduction orientation, such as at a 30 degree angle relative to one another, as noted above. The objective of this step is to position the patient's femurs in a consistent, repeatable, and comfortable manner relative to the robot 54. The desired position is to have the femurs neutrally lined up with the patient's hips so as to limit stress on the patient's upper legs and hips during a test and to create a repeatable and consistent orientation of the lower legs relative to the femoral epicondylar axes of the femurs of the patient.

At block 310, the patient's knees and the knee stabilizers 74 are centered relative to one another. In the disclosed example, as shown in FIG. 14, each knee stabilizer 74 is mounted on or to a support bracket 312, which is positioned under and coupled to the lower knee clamping element 78b. The support bracket 312 is mounted on an adjustment or slide track 314 that is carried by part of the RKT apparatus 50. In this example, the slide track 314 forms a cross-member traversing the rails 82 on the sub-frame 68. However, the slide track 314 can instead be a separate component mounted to the sub-frame 68, a cross-member 84, or another part of the RKT apparatus 50. The support bracket 312, and thus the knee stabilizer 74, is side-to-side adjustable along the slide track 314. The support bracket 312 and/or slide track 314 can incorporate a locking element 316 that is configured to selectively secure or release the knee stabilizer 74 relative to the slide track.

In the disclosed example, to center the knee stabilizers 74 on the patient's knees, one can release the locking elements 316, if not already done as noted above at block 300. Though not specifically described herein, the locking elements 316 can include a knob 318 that is manipulated to lock or release the knee stabilizers 74 relative to the slide tracks 314. The knee stabilizers 74, when released, can slide along the respective slide tracks 314. The knee stabilizers 74 can be moved side-to-side laterally or medially in order to center the corresponding posterior knee pads 79 on the lower knee clamping elements 78b under the knees of the patient. The construction of the support brackets 312, slide tracks 314, and locking elements 316 can vary considerably and still function as intended to provide side-to-side adjustability of the knee stabilizers 74. One objective of this step is to define a consistent and repeatable position for the patient's knees relative to the tibia positioning assemblies 90 generally in the X-axis direction. Another objective of this step is to center the patient's knees within the knee stabilizers 74 so that, when ultimately clamped onto the knees of the patient, each knee is centered among the pads 77 and 79 and thus securely retained in position to prevent movement of the femur and patella once clamped in the respective stabilizer.

At block 320, the thigh stabilizers 70 are adjusted and tightened to secure the patient's femurs in place. In the disclosed example, as shown in FIG. 15, each thigh stabilizer 70 has a primary mechanical adjustment device. The thigh stabilizer 70 is mounted to a positioning track 322 that is also carried on a part of the RKT apparatus 50. In this example, the positioning track 322 is a separate element that is mounted to the cross-member 84 at an end of the sub-frame 68. However, the positioning track 322 can instead be formed as a part of one of the cross-members 84 of the sub-frame 68 or can be formed as part of or be mounted on another part of the RKT apparatus 50. Further, each thigh clamping element 72 of one of the stabilizers 70 is carried by a truck 324 and each truck and thigh clamping element is mounted on and slidable along the positioning track 322.

In the disclosed example, each truck 324 can include a locking mechanism 326 that is configured to selectively secure or release each of the thigh clamping elements 72 relative to the positioning track 322. One can release the locking mechanisms 326, if not already done as noted above at block 300, and slide the thigh clamping elements 72 and trucks 322 along the respective positioning track 324. Though not specifically described herein, the locking mechanisms 326 can each include an actuator 328 that is manipulated to lock or release the trucks 324 relative to the positioning tracks 322. The construction of the trucks 324, positioning tracks 322, and locking mechanisms 326 can vary considerably and still function as intended to provide side-to-side adjustability of the thigh clamping elements 72. In one example, the actuators 328 can each function as a cam lock received in a bore 330 through the respective truck 324. Such a cam lock, when rotated in one direction, can be configured to secure the trucks 324 to the positioning tracks 322 and, when rotated in the opposite direction, can be configured to release the trucks allowing them to move along the positioning tracks.

As shown in FIG. 15, the trucks 324 and thigh clamping elements 72 can optionally be configured to include a secondary distinct mechanical adjustment device as well. This feature can aid in allowing the thigh stabilizers 70 to accommodate a wider range of patient leg sizes from small children to large adults. In this example, each truck 324 has a pair of receptacles 332 that are laterally spaced apart and open to the top surface of the truck. Each thigh clamping element 72 has a corresponding peg or pin 334 protruding downward from the body of the element. The pin 334 of each thigh clamping element 72 can be selectively inserted into either one of the two receptacles 332 in the corresponding truck 324. By choosing different receptacles 332, and without moving the trucks 324, the adjacent thigh clamping elements 72 on one of the thigh stabilizers can be mounted to the trucks in four different positional arrangements. Using the outer most receptacles 332, the thigh clamping elements 72 can be mounted further apart from one another. Using the inner most receptacles 332, the thigh clamping elements 72 can be mounted closer together. Using a combination of one inner receptacle and one outer receptacle, the thigh clamping elements 72 can be mounted in an intermediate spacing. Depending on which inner and which outer receptacle 332 is selected, the thigh clamping elements 72 can be shifted to the left or to the right, if desired or needed, also without having to move the trucks 324. This secondary adjustment device allows for greater versatility in setting up a patient. The aforementioned locking mechanisms, such as a cam lock type device, can be used to also secure the pins in the receptacles, if desired, or a separate retention means, if any, may also be used to retain the thigh clamping elements 72 to the trucks 324.

Once the patient's knees are correctly positioned, according to the step at block 306, the patient's thigh abduction angle is adjusted, according to block 308, and the knee stabilizers 74 are centered according to the step at block 310, the thigh stabilizers 70 can be adjusted, tightened, and clamped onto the patient's thighs. With the locking mechanisms 326 released, each thigh stabilizer 70 can be adjusted so that the respective thigh clamping elements 72 forcibly contact the sides of the patient's thigh. The locking mechanisms 326 can then be tightened, secured, or engaged to secure the thigh stabilizers 70 on the positioning track 322. Each thigh clamping element 72 should be positioned and each locking mechanism 326 tightened or secured such that the medial and later clamps apply substantially equal pressure to the thigh. One objective of this thigh clamping step is to permit a consistent and repeatable position for the patient's thighs relative to the tibia positioning assemblies 90. Another objective of this thigh clamping step is to then securely clamp the patient's thighs in place with thigh stabilizers 70. During testing, it is desirable that the femur position for each leg of a patient is securely retained to prevent lateral movement and femoral rotation once the thigh stabilizers 70 are adjusted and locked in place.

At block 340, each knee stabilizer 74 is clamped onto the patient's knee or patella. In the disclosed example, as depicted in FIG. 14, the framework 76 of each knee stabilizer 74 can include a pair of guide posts 342 on each side of the stabilizer. The guide posts 342 can be fixed to the upper knee clamping element 78*a* and can depend down from the element. Free ends 344 of the guide posts can be received in and slide through a corresponding pair of holes 346 on each side of the lower knee clamping element 78*b*. The upper and lower clamping elements 78*a*, 78*b* are adjustable vertically relative to each other, as noted above, by sliding the upper clamping element 78*a* and guide posts up and down relative to the lower clamping element 78*b*, which is fixed to the support bracket 312. A fixing screw 348 in this example extends transversely into each side of the lower clamping element 78*b* between the pair of holes 346. The fixing screw 348, when rotated in one direction can reduce the diameter of the holes 346 to clamp onto and lock guide posts 342 and, when rotated in the opposite direction, can increase the diameter of the holes to release the guide posts. With the guide posts 342 released, the upper knee clamping elements 78*a* (and guide posts 342) can be removed from the lower knee clamping element 78*b* so that the patient's knees can be readily positioned on the lower clamping elements, as noted above for the step at block 306. Once the knees are properly positioned after the step at block 306, the upper knee clamping element 78*a* can be replaced on the lower knee clamping element 78*b* any time before block 340.

At this point, the locking elements 316 on the knee stabilizers 74 are still released so that the knee stabilizers 74 are still free to slide or move along the slide tracks 314. Also at this point, the upper knee clamping element 78*a* should now be or should already have been reinstalled on the lower knee clamping element 78*b*. The upper knee clamping element 78*a* is then clamped downward so that the pads 77 on the upper knee clamping element press down against the patella of the knee. The downward clamping force should achieve a predetermined or desired force, such as 30 lbs., and equal pressure should be applied to both the medial and lateral sides of each knee stabilizer 74. The knee stabilizers 74 can then be secured in this clamping condition. In this example, the fixing screws 348 can be rotated to secure the guide posts 342. A force gage or other suitable method and/or device can be used to achieve or ensure the desired downward clamping force applied by the knee stabilizers 74 on each patella of the patient. Once the knee clamping elements 78*a* and 78*b* are clamped and locked, the knee stabilizers 74 can then be locked in place on the slide track 314 by actuating the knobs 318. In general, the thigh stabilizers 70 and the knee stabilizers 74 are secured before the Varus-valgus adjustment along the rail 314 is secured. When the knee stabilizer 74 is clamped down, such as with 30 lbs. of force, the side-to-side position of the knee stabilizers 74, i.e., the Varus-valgus adjustment along the rail 314 will settle into a position that the knee naturally seeks. Once this occurs, the locking mechanisms 316 can be secured to lock the side-to-side position of the knee stabilizers 74 along the rails 314. The objective of this knee clamping step is to securely clamp the patients knee at the patella with knee stabilizers 74. During testing, it is desirable that the lower end of the femur and the patella are securely restrained to prevent vertical movement at the patella once the knee stabilizers 74 are adjusted, clamped down, and locked. The aforementioned patellar sensor 73 on the upper clamping element 78*a* can detect residual motion in the patella during testing, which occurs even when the patient's knee is tightly clamped. The residual motion can then be accounted for and eliminated in the computation of joint play data and analysis of the knee joint. Other methods could be used instead of, or in addition to, the knee stabilizers 74 to apply this force, including but not limited to a spring system, a weight attachable to each of the upper clamping elements 78*a*, a screw mechanism, or the like.

At block 350, the soles of patient's feet are placed against the contact surfaces 94 and their heels are positioned against the heel stops 93 of the foot plates 92. In the disclosed example, the tibia positioning assemblies 90, via the sled assemblies 86 sliding on the tracks 80, are drawn toward the patient's feet by sliding the assembly along the tracks on the sub-frames 68. In an alternative example, the drive system may be stationary and only the foot plates 92 may be adjustable along the Z-axis to contact the patient's feet. Once the feet are in contact with the two plates 92, the tibia positioning assemblies 90 are in a testing position relative to the patient's feet and lower legs. When the feet are properly positioned, appropriate straps can be used to secure the feet to the foot plates. One objective of this step is to provide a consistent and repeatable procedure to properly position the tibia positioning assemblies 90 along the sub-frames 68 relative to a specific patient. Another objective of this step is to secure the patient's feet to the foot plates and thus to the drive system of the tibia positioning assemblies.

At block 360, the tibia positioning assemblies 90 are locked in place. In the disclosed example, each tibia positioning assembly 90 can be locked in the position achieved at the step of block 350. For example, once the patient's feet are properly positioned and then secured or strapped to the foot plates 92, the sled assemblies 86 can be locked in this position using the locking mechanisms 88. The locking mechanisms 88 can lock the sled assemblies to the rails 82 on the sub-frame 68 or to the tracks 80. Though not shown herein, in one example, a pin of the locking mechanisms 88 can penetrate a hole, groove, or slot on the rails 82 or the tracks 80. Securing or fixing the sled assemblies 86 in place will lock the tibia positioning assemblies 90 at the adjusted position accommodating the particular patient being set up.

Patient specific measurements can also be determined and recorded during set-up. In one example, a ruler 362 or other indicia or markings may be provided on or along one of the lengthwise parts of each sub-frame 68, such as along one of the rails 82 (see FIG. 6). The rulers 362 can be configured to identify the length of the lower legs of the patient being set up based on the position of the tibia positioning assemblies 90 along the tracks 80 or the sub-frames 68. This measurement can be recorded by the memory 206 for each specific patient and can then be utilized to set up the robot 54 for a particular patient each time the patient is tested and can be used for the analysis and diagnosis. This helps to ensure that the RKT apparatus 50 is set up the same way for the same patient. This also helps to ensure that the data is consistently obtained for different patients. The objective of this step is to aid in providing a fixed, consistent, and repeatable set-up position for the tibia positioning assemblies for each patient.

At block 370, the patient's feet are rotated to a desired initial rotational orientation to begin testing. In the disclosed example, each foot plate 92 can be manually rotated to a desired position determined by the orientation of a part of the patient's foot or a part of the foot plate. For example, the patient's foot could be positioned with the toes up and perpendicular to the floor beneath the RKT apparatus. More specifically, the starting orientation may be to orient the second toe on each foot to point vertically or perpendicular to the floor. This initial foot rotation position can instead be established by moving the Z-axis motor 160 into a neutral zero-torque position, as described in more detail below, to find a true neutral resting position for the patient's feet. Once the desired initial position is reached, a command can be sent to the motor to hold the position until testing proceeds. The objective of this step is to define a consistent and repeatable starting orientation for the foot plates 92 and thus the patient's feet.

At step 380, each tibia rod device 96 is positioned under the patient's calves. In the disclosed example, each tibia rod device 96 can be length adjustable to retract or extend the calf plate 100 to a desired position under the corresponding calf of the patient. Once in the desired position, the calf plate is in a testing location or an AP test location relative to the patient's leg. Another patient specific measurement can be utilized to repeatably and consistently position the calf plate. In one example, a second ruler 382 or other indicia or markings may be provided along part of the tibia rod device 96 to help determine the proper or desired position for the calf plate 100 (see FIG. 6). For example, the slider segment 98b of one of the tibia rods 98 can include the ruler 362 or markings that correlate with the ruler 362 on the tibia positioning assemblies 90. If the desired position of the calf plate 100 for each patient is to be three-quarters (¾) of the way up the leg from the patient's heel, the ruler 382 can be a ¾ scale version or equivalent of the ruler 362, which defines the patient's leg length. Thus, by selecting the same measurement on both rulers 362, 382, the position of the calf plate 100 is assured to be at ¾ of the length of the patient's lower leg on each tibia positioning assembly 90 for the patient. Such physical measurements help to ensure that the patient set-up is as consistent as possible. The objective of this step is to provide a mechanism to ensure repeatable and consistent positioning of the tibia rod device 96 so that the AP test is always conducted at the same relative location on each patient's legs.

At block 390, one or more of the aforementioned tibial or translation sensors 210 are placed on the patient's legs at predetermined locations. In one example, the sensors 210 can be positioned on the flat region of the bone that is just medial to the tibia tubercle on each leg. The translation sensors 210 are then strapped into place or otherwise securely held in the patient's legs at the selected location. The aforementioned location may be selected for the sensors 210 because this region has the least amount of soft tissue between the sensor and the bone. This location will thus help during testing to limiting the degree of movement of the sensors 210 caused by the soft tissue moving relative to bone. In one example, round sensor holders can be used to retain each sensor 210 in order to inhibit or prevent the sensors from rocking, due to compression of the calf muscle or movement of other soft tissue during testing. The purpose of this step is to position translation sensors 210 on the legs of the patient whereby the precise position of the sensors is tracked by the tracking system 208 during testing.

At block 400, the RKT apparatus is operated to perform one or more of the AP, VV, and rotation tests on the patient. Once the robot 54 is set-up and once the patient is set-up relative to the robot, knee testing and evaluation procedures can be run according to the operational parameters of the robot, including the X-, Y-, and Z-drives and according to the programming of the computer. The purpose of this step is to obtain data, information, and feedback that are recorded from the tests and determined or analyzed by the computer.

The foregoing set-up procedures can be further enhanced or altered in any number of ways. Also, the disclosed analysis system 200 and the RKT apparatus 50 can also be altered or enhanced in a number of ways. Additional set-up procedures can be performed and/or utilized prior to or during testing. A number of examples are described below according to the teachings of the present disclosure.

In one example of additional set-up procedures, though not mentioned above, additional rulers or other indicia or markings can be provided on other parts of the RKT apparatus 50 to indicate specific measurements and/or to indicate specific positions of particular parts of the robot 54 after setting up a specific patient and the robot for testing. For example, rulers can be provided on the thigh stabilizers 70, such as on the positioning tracks 322, and/or on the knee stabilizers 74, such as on the slide tracks 314 and/or guide posts 342. In another example, a ruler can be provided on a portion of the tibia positioning assemblies 90, such as on the pivot plate 150, to indicate the Varus-valgus starting position and linear or angular distance traveled during the Varus-valgus test. In yet another example, a marking scale may be provided on a portion of the Z-axis drive to indicate the position of the foot plates 92. Any such markings, indicia, or rulers can be used to set-up the patient or the robot 54 or to record specific set-up parameters, once set-up for a given patient that are repeatable from test to test each time the patient is set up for testing.

In another example of additional measurements to be taken, recorded and stored, during AP testing, measurements can be taken to help define the set-up position of the knee. Such measurements can include a measurement of the AP width (X-axis direction) of the femurs of the patient using points on the knee clamping elements. Other such measurements can include a measurement of the width or length of the tibia or femur using anatomic points collected using the electromagnetic tracking system. Another such measurement can include a measurement of the AP distance between the center of the distal femur and the center of the proximal tibia. Yet another such measurement can include a measurement of the distance between the tibia tubercle and the top of the knee or top of the patellar clamping element 78a as defined by the electromagnetic sensor positions or by points collected using the electromagnetic tracking system.

In another example of additional set-up procedures, such measurements can also include determining the initial or neutral position of a patient's knees at the time of setup to identify existing structural issues, such as a torn PCL. One possible indicator of, for example, a PCL tear can be an increased distance between the tibia tubercle and the top of the knee or patellar clamping element 78a. Another indicator can be the relationship between multiple measurements. For example, if the AP distance between the tibial tubercle and the top of the patellar clamping element is larger than a certain threshold percentage (i.e. 20%) of the AP width of the femur, that difference may indicate an injury to the knee or PCL. These types of measurements taken at initial set-up can be used to calibrate or shift the resulting data (i.e. load deformation curves) in order to account for side-to-side differences between the knees that could result from an injury such as a PCL tear.

Figure 16:
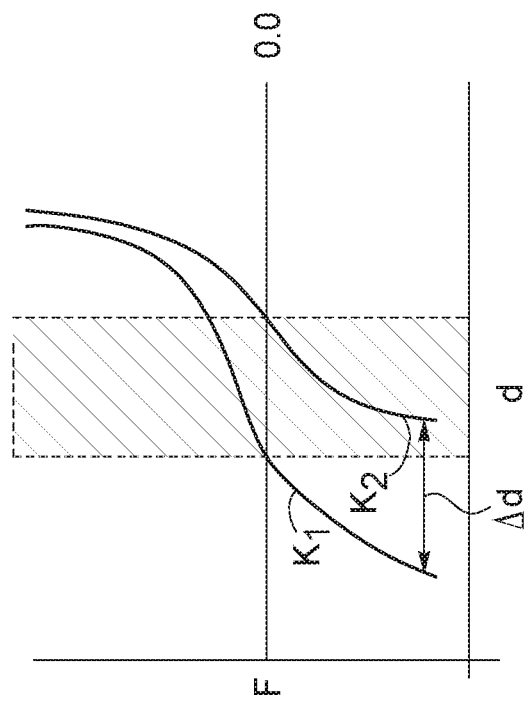
FIGS. 16 and 17 show two examples of test data feedback in graphical form that can be produced by the disclosed RKT apparatus in the environment of FIG. 10.
Figure 17:
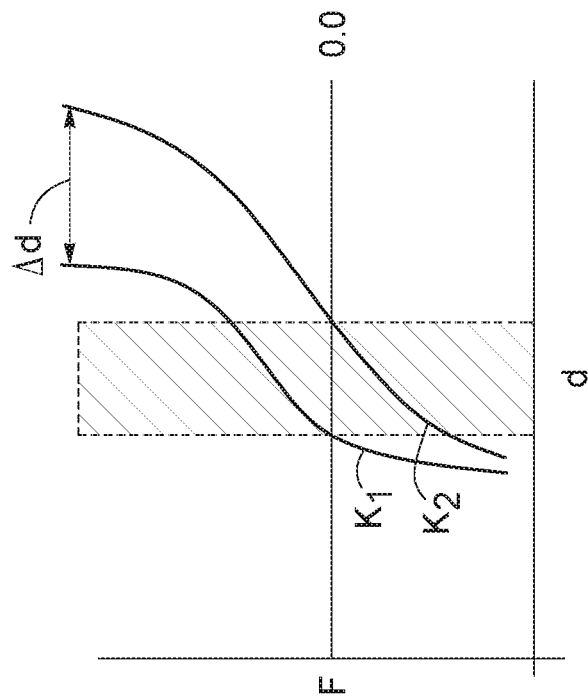

For example, as shown in FIGS. 16 and 17, an injury to one knee can quite significantly alter the force-travel curve produced during a test relative to the other knee. In FIG. 16, one knee K1 has an injury that results in a shift in the neutral or 0.0 force or torque position of the knee in comparison to the other healthy knee K2. The test being conducted (rotation, AP, or VV) and the force direction in which the neutral position of the knee has shifted can provide a strong indication as to which knee structure or ligament is damaged. The larger difference in the displacement or travel distance Δd between the two knees at the maximum applied force can also provide an indicator as to the type of injury or the degree of the injury to that specific structure or ligament. In FIG. 17, one knee K1 is relatively healthy in comparison to the other knee K2, but in this example, the larger Δd occurs in the opposite direction of movement during a test in comparison to the knees tested in FIG. 16. This indicates a different injured structure or ligament than does FIG. 16, if both curves are for the same type of test, such as a rotation test, an AP test, or a VV test on the patients' knees. The concept of neutral position is discussed in greater detail below.

In another example, an additional initial set-up procedure can include, during AP testing, employing one or more straps to secure the patients legs to the tibia rod devices 96. This may be to ensure that the tibia rod devices 96 can both push up in an anterior direction on the patient's legs and pull down in a posterior direction on the patient's legs during testing. Once the AP test is completed, these straps may be removed and the tibia rod devices 96 may be moved out of the way prior to conducting a rotation test or a VV test on the patient.

In yet another example of an additional set-up procedure, during a Varus-valgus or VV test, additional pads can be pushed into the knee stabilizers 74 between the medial and lateral sides of the patient's knees and the framework 76. Such pads may help to minimize medial or lateral movement of the knee under the clamp and minimize axial rotation during the Varus-valgus test. These added pads can be removed when the VV testing is complete. Alternatively, and as described above, adjustable pads 75 can be provided as a part of the knee stabilizers 74. These pads 75 can be adjusted and advanced inward to contact the medial and lateral sides of the knee during a VV test to inhibit rotation in the knee during testing. These pads 75 can be retracted or withdrawn when the VV test is complete and for performing other tests.

In still another example of additional set-up procedures, the electromagnetic tracking system 208 can be used to define a set of robot based and anatomical based coordinate systems. These additional coordinate systems can be helpful to obtain additional and useful data from testing of patients and to provide more accurate and meaningful data and diagnostic information. The coordinate systems can be used to more accurately determine the relative rotation or movement between two bones. Each bone should have a coordinate system that can be related to the other and to a coordinate system of the robot. For example, AP motion is typically defined to occur along the Y axis and internal-external axial rotation is defined to occur about the Z axis, as noted above. In order to make an orthogonal coordinate system, the X axis must be created in relationship to the Y axis and Z axis and each must be perpendicular to the other. Flexion-extension around a created X axis, however, may not accurately represent the true or actual flexion-extension axis for that knee. Thus, a non-orthogonal coordinate system may be chosen in order to force knee motions into a clinically friendly space. This can result in some motions between two bones becoming hidden by or added to one of the non-orthogonal or orthogonal axes. A better method is disclosed below for determining useful and more accurate coordinate systems.

For setting up the coordinate systems, first, a robot based world coordinate system 230, as depicted in FIG. 18, can be defined based on the location of the transmitter 214 of the tracking system 208. The world coordinate system 230 is fixed and does not move during testing. However, the location of the transmitter 214 can vary or it can be fixed in a specific location and calibrated for the robot or clinical examination system. The transmitter 214 can be configured to locate and track the position of the translational sensors 210 throughout testing. The sensors 210 are strapped to the proximal ends of the patient's tibias. Each sensor 210 is placed on the medial flare of the proximal tibia so as not to interference with the robot 54 and because this region has a very low skin to bone ration. The positioning of the sensors 210 can be tracked relative to the fixed location of the world coordinate system 230. Using the aforementioned circular sensor for the translation sensors 210 can be particularly useful for consistency during testing because circular sensors have no corners or protruding edges that deforming skin or soft tissues can push against during testing. This may be important during AP testing when the calf is deformed by the straps used to secure the calf to the tibia rod devices 96.

The translational sensor 210 on each leg of the patient can also be used in defining a local coordinate system for each leg. A tibial coordinate system 240, as depicted in FIG. 19, can be defined for each tibia based on the tracking system 208. The relationship between selected anatomical landmarks on the patient's legs and the translation sensors 210 on each tibia can be calculated, recorded, and stored in the memory 206. The electromagnetic tracking system 208 includes the aforementioned pointer 212, which also has a position sensor. During patient set-up, the pointer 212 can be used to identify the selected anatomical landmarks. The pointer 212 can be placed on each selected bony landmark on both of the patient's tibias. In a particular example, the pointer 212 can be used to identify points taken at the tibial tubercle, the AP midline of the medial tibial plateau and the lateral tibial plateau, the medial-lateral (ML) midline of the anterior proximal tibia and posterior proximal tibia, and the AP midline of the medial malleolus and the lateral malleolus relative to the sensors 210 on each leg of the patient. The location of the sensor of the pointer 212 is then used to calculate, record, and store the position of each landmark relative to the sensors 210 and/or the transmitter 214. Each of these anatomical landmarks can thus be used to define the tibial coordinate system 240 for each of the patient's tibia. The origin of each tibia coordinate system 240 can be defined as the midpoint between the respective points taken from the aforementioned medial and lateral tibial plateaus. The position of the origin may be adjusted anteriorly or posteriorly based upon the AP thickness of the proximal tibia or the position of the point taken on the tibial tubercle. In the end the origin should be found to be 50% of the width of the proximal tibia and 50% of the thickness of the proximal tibia at a distance just distal to the joint line along the length of the tibia.

The Z axis of each tibial coordinate system 240 is defined using a vector from the respective tibial origin to the midpoint of medial and lateral malleoli. The Z-axis vector should point from the above described tibial origin towards the foot to the mid-point of a line between the medial and lateral malleoli. The Z-axis could also be adjusted using points taken along the anterior tibial crest such that a new Z-axis is formed parallel to these points. At initial set-up, the Y axis can be defined as parallel to the second toe of the patient's foot, and perpendicular to the posterior pad 79 on the knee stabilizer 74. The defined Z-axis forms the core of the calculations necessary to describe a perfectly orthogonal tibial coordinate system. The cross product of the above defined Y-axis and the above defined Z-axis produces an X-axis that is perpendicular to the plane of the Z and Y axes. The cross product is then taken between the above defined Z-axis and the new X-axis to produce a new Y-axis. The Z-axis remains in its original position while the new X-axis and Y-axis are constructed around it. These appropriate mathematical vector operations can be used to determine the axes of each of the tibial coordinate systems 240 such that they are an orthogonal coordinate system. In the above method the Z-axis remains the core of the tibial coordinate system such that the X-axis and the Y-axis are moved to attain orthogonality. Another alternative method could make the above Y-axis the core of the tibial coordinate system while, first the X-axis is constructed followed by the Z-axis to attain orthogonality. The tibial coordinate systems 240 can then be related to the recorded motion of the rotations sensors or torque transducers 118, 148, 168 and the translational sensors 210, as well as to the world coordinate system 230, during testing.

A femoral coordinate system 250 can also be defined for each leg of the patient. In one example, the pointer 212 can be used to define a machine-based femoral coordinate system for each leg. The pointer 212 can be used to identify three points on the robot, such as on the center of the upper clamping element 78a and two points on the lower clamping element 78b of the knee stabilizer 74, one medial and one lateral along the plate of the knee stabilizer 74. The origin of the femoral coordinate system 250 for each leg can be defined as the center of the triangle at the AP midline of the two lower points. This origin is unique in that the patient has the distal femur clamped by the knee stabilizer 74 and thigh stabilizer 70. The distal femur is positioned such that the posterior condyles are resting on the lower clamping element 78b and that the patellar clamp above, i.e., the upper clamping element 78a is compressed down upon the patella pushing the patella into the trochlear groove. This influences the distal femur to move medially or laterally on the lower clamping element such that the origin of the femur moves medially or laterally under the compressed patella. Care is taken to position the distal femur such that the epicondylar axis of the distal femur is parallel to the two points taken along the lower clamping element 78b of the knee stabilizer 74. The ability to track the amount of femoral abduction or adduction during patient setup helps to insure symmetrical placement of the distal femur such that the epicondylar axis is parallel to the aforementioned points.

The Y-axis is taken as perpendicular to the pad 79 of the lower clamping element 78b on the knee stabilizer 74, suggesting that it is perpendicular to the posterior femoral condyles after patent set-up. The X-axis is taken as parallel to the pad 79 of the lower clamping element 78b and to the two distal points on the front of the lower clamping element such that it is aligned with the epicondylar axis of the distal femur after patient set-up. The epicondylar axis of the femur is essentially parallel to the distal femur joint line in the healthy knee. The X-axis is then taken as the core of this femoral coordinate system construction. The cross product of the X-axis and the Y-axis is taken to construct a Z-axis that is perpendicular to the plane containing the above X and Y axes. The cross product is then taken between the Z axis and the X axis to produce a new Y axis. Appropriate mathematical operations are used to construct the orthogonal femoral coordinate system for each distal femur. An alternate method to construct the distal femoral coordinate system would be to use the above method using the proposed Y axis as the core vector with construction of first the Z axis and then the X axis. The femoral coordinate systems 250 can then also be related to the recorded motion of the rotations sensors or torque transducers 118, 148, 168 and the translational sensors 210, as well as to the world coordinate system 230 and tibial coordinate systems 240, during testing.

In the disclosed example, the Z axes for the tibias is independent from the Z axes for the femurs. This is because during testing a clinician will anchor the femur and "watch" the motion of the tibia relative to the femur. In other words, the movement of the tibia is "watched" from the femur toward the top of the tibia. Since movement of the tibial plateau surface is important for a knee examination, a view perpendicular to the tibial plateau surface may be preferable for examination. As a result, for the disclosed set-up procedure of defining coordinate systems, the Z axis of the femur must be parallel to the epicondylar axis of the distal femur such that relative motion of the tibia around the Y axis of the femur represents abduction and adduction of the tibia with respect to the distal femoral epicondylar axis. This replicated or projected Z axis is has an unknown relationship to the actual mechanical axis of the femur and is used to better represent the joint play at the level of the distal femur and the proximal tibia. The only way to determine the actual rotation center of the femoral head, without an invasive procedure, is to mathematically estimate or predict its location. A relatively significant statistical error of about 2.5 cm has been determined from test to retest when using mathematical estimation techniques. Thus, using the distal femoral epicondylar axis to produce the femoral Z axis provides a reasonable estimation but without the significant mathematical error. Another alternative method could utilize the tibial Z axis to construct the femoral Z axis. However, this may make the patient set-up critical in that the tibia must be set-up such that it is aligned with the mechanical axis of the femur at set-up. This could be done using a laser pointer resting at the second toe on the foot holder such that during set-up the point passes above the center of the knee and past the anterior superior iliac spine during set-up. This would result in utilizing the constructed tibial Z axis from the proximal tibia and the medial and lateral malleoli, which uses the most consistently measurable anatomical features of both limbs. It is possible, however, to use a different Z axis for the femoral coordinate systems or to define the axis in different ways. It is also possible to define either or both the tibial and femoral coordinate systems using different anatomical or robot points and/or other techniques.

The definition of the above mentioned coordinate systems 230, 240, and 250 provides two methods to compare test data and to view the examination. The first method relies upon the set-up alone, as described above, for comparing movement in the right tibia to movement in the left tibia. The first method can be studied from two different perspectives or fields of view. The first is from a global perspective or world view, as represented in FIG. 18. This world view provides a perspective that includes the overall lower body of the patient including both legs, such as if sitting at the head of the bed and watching examinations of both the right knee and the left knee at the same time. Each knee moves in space and such movements are recorded from the world view perspective. The data from the world view of the motion of each leg can be compared. The second field of view is from a local perspective for each leg separately from the femur of the right leg and from the femur of the left leg, i.e., the femoral view, as represented in FIG. 19. This field of view provides a local perspective that includes one leg at a time, such as if sitting on each distal femur and viewing the movement of the each tibia with respect to the ipsilateral femur separately. The data from the femoral view of the motion of each tibia can be compared, though one should keep in mind that the right and left leg motions are mirror images of each other. The accuracy of this method depends upon the ability to set-up each femur in an identical but mirror opposite position in the world view. As described, each tibia (right and left) can have an initial equilibrium position at set-up. During patient set-up this equilibrium position or state can be considered a unique feature of each tibia and can be recorded for the later evaluation.

The second method for comparing the right leg and the left leg of the patient utilizes the aforementioned anatomical points that can be recorded during set-up. Each set of anatomical points that were recorded can define a means to determine the anatomical position of the tibia and femur utilizing the tibia and femoral coordinate systems described above for each leg. Thus, when measuring a side-to-side difference in AP translation between the femur and the tibia, the relative translation between anterior patella and anterior tibial tubercle can be used for consistency and reduction in error. For tibial axial rotation, the malleolar axis can be used for side-to-side comparison utilizing an anatomical measure for consistency and reduction in error. If symmetrical abduction of each femur is obtained at initial setup, then Varus-valgus testing can also be consistent and reduce error.

There are benefits to obtaining and utilizing both of the aforementioned world and local fields of view in determining various aspects of the health of a patient's knees. Side-to-side differences have been used for decades to compare an injured knee to a healthy knee. However, this method can be flawed due to the wide variance in laxity in normal knees and the fact that the reportedly healthy knee may have been damaged at some point, but is not symptomatic at the time of the testing. The world view is useful in this situation where a side-to-side comparison could be misleading. By also using free body kinematics in analyzing the data collected during testing, one can calculate relative motion between the tibia and femur in 3D space without any restrictions on the motions that might otherwise exist in the prior known methods. The disclosed set-up procedures allow more accurately defining the motions of the knee joint compared to existing systems. The combination of using 1) a robotic testing device, 2) an electromagnetic tracking system, 3) sensor or robot based coordinate systems, 4) anatomical coordinate systems that are tracked relative to the sensor-base coordinate systems, 5) free body kinematics to analyze the motion data, 6) a world view of both knees, 7) a local view of each tibia moving relative to the respective femur, and/or 8) consistent set-up procedures provides significantly improved joint testing and evaluation.

In another example of additional set-up procedures, a concept of neutral position, torque zero, or force zero can be quantified for a given patient and then applied during set-up or after initial set-up but before testing is completed. When testing a patient's knee laxity in an instrumented or robotic device such as the disclosed RKT apparatus 50, the definition of a zero point may be important as it can correctly provide a base reference to accurately define the extent of motion in any direction or about any axis of testing. How the patient is set up in the RKT apparatus 50, the actual physical structure of the patient's legs and condition of their knees, and how a test is run will determine the zero point.

The disclosed torque sensors 118, 148, 168 are useful in providing more specific information to the clinician than other known testing methods and devices. Use of the disclosed torque sensors 118, 148, and 168 also allow for greater consistency in setting up the patient and the robot 54, as well as during testing. Using the rotation test as an example, significant differences in torque are evident during patient set-up where the second toe is placed vertically, i.e., in the aforementioned toes up orientation to start the test. For example, a patient who has naturally externally rotated legs would require a much higher torque just to rotate their tibia to the toes up position. However, as noted above, this toes up position is the robot defined zero point or initial position. Using this position for a naturally external rotated patient could yield a false impression of the extent of rotational motion.

The above described motor 160 reverses direction based on achieving a maximum recorded torque value during a rotation test. Thus, the rotation test for this patient would not achieve much additional internal rotation because there would be a residual torque or force already required simply to reach the toes up initial robot starting position. In other words, internal rotation would not go very far beyond the toes up position before the motor 160 perceives the maximum torque value and reverses direction toward external rotation. Accurately distinguishing between external and internal rotation has been a problem with prior known methods and devices. As a result, the two motions are often combined into a total rotation value, which is not as useful for defining the condition of the knee.

The disclosed torque sensor 168 can thus provide a method to accommodate for this issue and to permit a clear distinction in the recorded data between external and internal rotation. This can be done by defining a new torque zero point for each knee of a patient, based on taking initial torque measurements of each knee. The starting rotation position of the tibias can then be adjusted from the initial robot toes up starting position to an actual zero torque or neutral position for each knee. This position might be different for each knee of the patient, and differences between knees in this zero torque position could be clinically meaningful. The orientation of the foot plates 92 can be shifted to a position for each knee whereby the actual torque at the sensor 168 is equal to 0. This can allow the actual neutral point to be utilized for each leg to give a more accurate representation of the true extent of external and internal rotation.

These same zero torque or neutral position concepts can be applied for Varus-valgus testing and anterior-posterior testing. With regard to AP testing, when the tibia rod devises 96 are strapped to the legs of the patient, there may be residual torque in the X axis motor 110 detected by the torque sensor or transducer 118, similar to rotation. The starting point of the motor 110 can be adjusted to the actual zero torque or neutral position for each knee of the patient. With regard to Varus-valgus testing, there can also be a residual VV force in the motor 140 detected by the torque sensor or transducer 148, based on the alignment of the patient's legs. The starting point of the motor 140 can thus also be adjusted to the actual zero torque or neutral position for each leg of the patient. Alternatively, or in addition, for Varus-valgus setup, a linear bearing can be positioned under the knee stabilizer 74 that can allow for still finer adjustment of the Varus-valgus alignment in each leg. The torque sensors or transducers 118, 148, 168 can be used during set-up or prior to testing to adjust for any patient anatomic variance from the initial set-up parameters.

Analysis of the data can play an important factor in the management of error during knee laxity testing using a robotic system. Data collected can be presented as a series of positive and negative peak torques and positions for maximum internal and external rotation from each test cycle (see FIGS. 16 and 17 for generic examples). A load-deformation curve can be constructed from a single test cycle or from two or more test cycles. The curve can represent one of the test cycles, such as a third cycle of three test cycles, which might typically offer the best data from three cycles. Instead, the curve can represent an average of multiple test cycles, matching torque and position from each test cycle. Position may be calculated from the right and left femoral view with an appropriate mirror image transformation such that the left side can be compared to the right side. In one example, a right hand coordinate system can be applied to the left knee so that positive motion on the X axis is lateral translation, on the Y axis is anterior translation, and on the Z axis is distraction. Similarly, positive rotation around the X axis is flexion, around the Y axis is valgus, and around the Z axis is internal rotation. A mirrored system can be applied to the right knee such that the same rotations and translations exist for the same directions of the left knee.

Particular attention can be paid to the definition of the zero position in the knee, as noted above. The zero torque or neutral position of the knee defines the extent of internal versus external rotation, anterior versus posterior translation, and Varus versus valgus rotation. Thus, neutral position can be a key biomechanical descriptor, and if chosen poorly, can introduce significant error into the analysis and results of testing. If both the ACL and the PCL are damaged in one knee to different degrees from an injury, it can be very difficult to determine which and how much the ligaments have been compromised. Without a world view, or a reference view, one cannot determine if one or two or more ligaments have been damaged, only that damage has occurred. In the knee, the world view provides a reference to determine which ligament was injured and by how much.

Utilizing the zero or neutral position at set-up can help determine the extent of damage and to which ligament or ligaments. It is desirable that peak positive torque/load be matched with peak positive position and peak negative torque/load be matched with peak negative position in order to properly represent the load-deformation curve for a given knee of a patient. These maximums and minimums in the load-deformation curve are fixed references in the world and femoral views. The neutral position and zero torque will automatically be determined in this situation. The clinician does not have to pick or estimate those conditions, as the zero or neutral position and zero torque conditions will define themselves. Employing this concept during testing removes bias and error that may otherwise be introduced if the zero point for position or torque/load is picked by the clinician.

In another example, a neutral position of the patient's legs can be accounted for in the data output by taking into account the initial residual torque detected at set-up and shifting the data accordingly. This would eliminate the step of further setting up the patient to account for any differences in initial set-up and actual zero torque or neutral positions in the rotation, AP, and VV tests. In another example, a neutral position of the tibia in anterior-posterior testing can be defined using the position of the tibial tubercle on each leg of the patient. The tubercle will likely be more posterior in a patient that has a torn PCL. This information could be used to adjust motor starting position or in shifting the AP load-deformation curve in the output data accordingly. This would be beneficial because the injured knee would appear to have very little posterior translation due to the fact that the unadjusted zero point would be more lateral caused by the sag of the leg as a result of a torn posterolateral corner complex (PLC).

In another example according to the teachings of the present disclosure, the previously described concepts of patient set-up, robot set-up, defining coordinate systems, recording measurements, and/or determining zero torque and/or neutral or zero position can help to describe, determine, and ultimately evaluate two additional new concepts: equilibrium position and new extent. These concepts can be useful in analyzing the injury to the patient's joint and in determining a course of action to repair the injury and/or to restore the damaged joint.

The first concept is equilibrium position, which for a normal knee represents the natural position of the knee based on the joint bone structure and the resultant forces of all the ligaments and muscles across the knee. The normal knee also has a characteristic joint play or joint unimpeded motion at a set position of the joint in which the bones of the joint move with respect to each other around the normal resting or natural equilibrium position at the set position. For evaluating knee-joint play, testing should be done without influencing the natural relative position of the tibia with respect to the femur. Care should be taken during set-up to determine and document or record the initial position or datum for the entire leg. In essence, this initial position of the whole leg (i.e. degree of hip and knee flexion, hip abduction and supine positioning) identifies the equilibrium state of the ligaments, which is when the tension in all intact ligaments between the tibia and the femur sum to zero taking into account gravity at the position of evaluation. Ligaments that are torn will have an influence on this initial position. When a ligament is torn and its restraining energy/force is lost or altered, there is a shift to a new initial or equilibrium position in the knee. It is the absolute and relative location of the tibia in this new equilibrium position that may provide the clinician with important clues as to the injury. An incorrect diagnosis of the injury can result if the initial or equilibrium position is not taken into account during the analysis.

The second concept is the new extent or new total range of motion of the knee after a ligament injury. The new extent is based on the new equilibrium position that has changed after an injury to a ligament and any changes in extent that occur as a result of this ligament injury. The joint play in the injured knee may be different than before the injury or may be the same as before the injury. However, the joint play in the knee starts from a new position, i.e., the new equilibrium position. For example, a normal knee may have a total combined motion of 20 degrees of rotation, which might be broken into 10 degrees of external rotation and 10 degrees of internal rotation. The equilibrium position for rotation would be at neutral or 0 degrees of rotation in this example. If a ligament is injured, the equilibrium position of the knee relative to rotation will shift. If the equilibrium position shifts to 5 degrees of external rotation then the new "neutral or 0 degree position" becomes that old 5 degrees of external rotation. As a result, if it has the same total range of motion of 20 degrees, the knee would have 15 degrees of internal rotation and 5 degrees of external rotation. In other words, the injured knee may not have the same amount internal and external rotation as before because the equilibrium position has shifted. Currently, the change in equilibrium position that occurs in an injured knee is often not taken into account by a surgeon during treatment of that knee. The results can be less than satisfying to the patient.

Comparison of load-deformation curves for knee evaluations may occur, either from side-to-side (left knee to right knee) in a single patient or across a population of patients. When comparing curves, it may be tempting to register or align the curves to a specific point, such as torque 0 or position 0, and overlapping each curve relative to that point. It is not uncommon for a clinician to look at load-deformation curve features to find a common point of comparison between limbs or between subjects. For example, the inflection point in a load-deformation curve might assumed to be torque 0 or position 0 for that limb. However, this is often not the case. Cumulative error exists at any point in the load-deformation curve. When the clinician focuses attention on one point as being more important than another along the curve, any error at that point is propagated throughout the entire load-deformation curves. Most load-deformation curves have a long center section with two asymptotic sides (see FIGS. 16 and 17). These asymptotic sides indicate the increasing torque/load as the ligament tightens and movement becomes more restrained or limited. The center, flat portion of the load-deformation curves indicates that a small amounts of torque can produce large changes in position in the joint. It is the characteristics of this central section of the curve that should make the researcher wary of choosing zero position or zero torque independently of the data. By choosing points at the ends of the load-deformation curve, large changes in torque produce little changes in position. Less error would be introduced into the testing process when using the endpoints of the load-deformation curve as a reference point rather that the central region.

Figure 20:
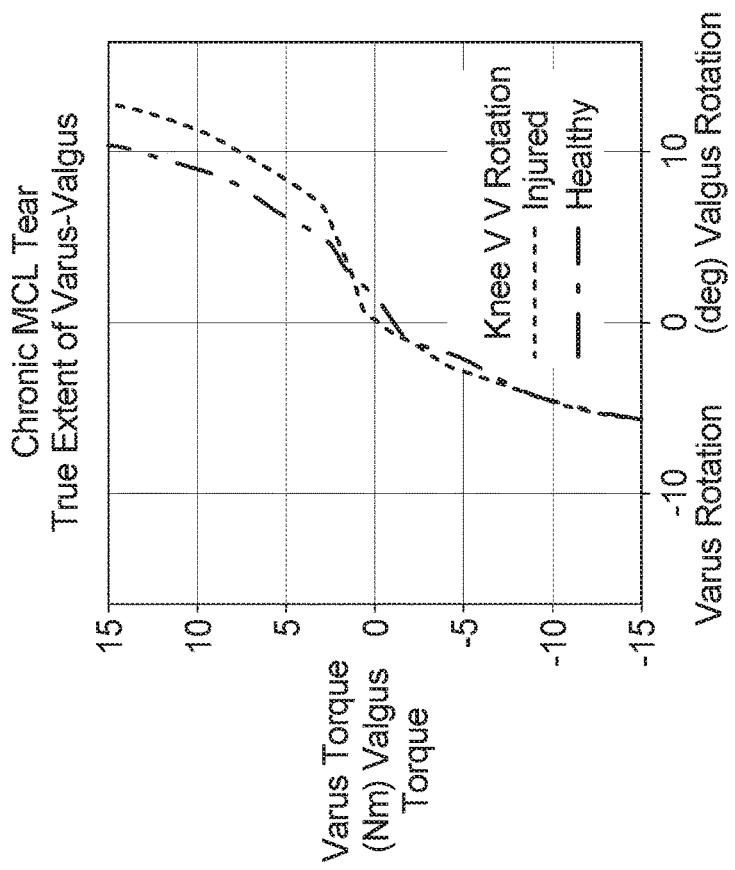
FIG. 20 shows one example of a load-deformation curve where equilibrium position of the knee is not accounted for in the data.
Figure 21:
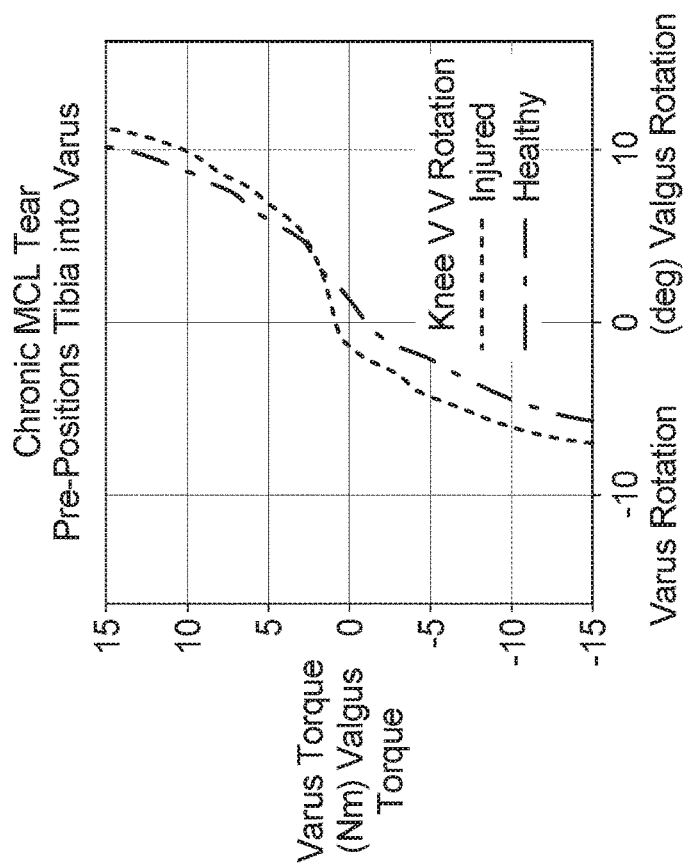
FIG. 21 shows a load deformation curve for the data of FIG. 20 but taking equilibrium position into account.

When a load-deformation curve is constructed from data produced during knee laxity testing with the RKT apparatus 50, the curve is produced in reference to the initial position of the tibia with respect to the femur at set-up. With the tibia as an intercalary bone sitting independently between the femur and the talus, the tibia can find its own equilibrium position. This position can be the result of a damaged or torn ligament, i.e. a posterolateral corner injury will leave the tibia in a recurvatum position. Thus, it can be confusing to compare the load-deformation curve of a normal or healthy knee with that of an injured knee because of the new natural or equilibrium position caused by the damaged ligament(s). The load-deformation curve in the injured knee is a combination of the new extent or range of motion and the new equilibrium position of the tibia with respect to the femur. In a patient with an MCL injury, the new equilibrium position of the tibia with respect to the femur would be shifted to a more valgus position than the healthy knee. Testing from this position may create the illusion that the tibia moves more into Varus than the opposite leg (see FIG. 20). When the difference in initial conditions, i.e., differing equilibrium positions, are eliminated or accounted for in a side-to-side comparison, the actual difference in new extent becomes readily apparent (see FIG. 21). In this example, the patient has significant MCL laxity with valgus loading.

FIG. 11 illustrates a simplified view of the disclosed analysis system 200, which can be directed to computation and evaluation of joint equilibrium position and new extent.

In this example, the analysis system 200 includes a robot apparatus for joint evaluation and testing, such as the RKT apparatus 50 disclosed herein. However, the robot testing apparatus can differ from the RKT apparatus and can instead be for evaluating other types of joints, such as ankles, elbows, shoulders, or the like. The analysis system 200 also includes the electronic components, such as the computer 202, the memory, 206, and the processor 207. However, the electronic components can also differ from the disclosed computer, memory, and processor and yet function as intended. The computer 202 may be a workstation, laptop, mainframe, tablet, handheld device, or cloud based system that is coupled to the RKT apparatus. In the disclosed example, the processor 207 is in communication with the RKT apparatus, and particularly with the robot 54. In this example, the communications and coupling between the RKT apparatus 50 and the computer 202 are directed to providing data acquired by the robot 54 to the computer. Alternatively or additionally, the communications are directed to allowing the computer 202 and/or the processor 207 to control one or more aspects or features of the RKT apparatus.

The processor 207 is configured through execution of the input instructions 218 to obtain the rotational and translational motion data and torque or load data captured via the robot 54. In some cases, the input instructions 218 can cause the processor 207 to request the rotational and translational motion and torque or load data from the robot 54. In other cases, the data may be received (e.g., provided) without a request. For instance, the input instructions 218 may cause the processor 207 to access the memory 206 to obtain the translational and rotational motion and torque or load data.

The rotational and translational data may thus be obtained in additional and/or alternative ways. For instance, the processor 207 may be configured to obtain raw sensor data from the RKT apparatus 50 for the rotational and translational joint testing. The input instructions 218 (and/or other instructions) may then cause the processor 207 to process the raw sensor data to develop rotational data indicative of the range of rotational motion, translational data indicative of the range of translational motion, and torque or load data indicative of the range of force applied relative to the range of rotational and translational motion. The extent to which the data provided to the processor 207 is processed before analysis may vary.

The input instructions 218 may cause the processor 207 to obtain rotational and translational motion data and torque or load data for various types of rotational and translational joint testing. In one knee-based example, the input instructions 218 configure the processor 207 to obtain rotational data indicative of external-internal rotational movement of the knee and rotational data indicative of Varus-valgus rotational movement of the knee. Fewer, alternative, or additional rotational data may be obtained. For example, the rotational data obtained may be indicative of Varus-valgus rotational movement. In the one knee-based example, the translational data is indicative of anterior-posterior translational movement of the knee. Alternative or additional translational data may be obtained. For example, the translational data may be indicative of movement along a different direction or axis than the direction or axis along which anterior-posterior movement occurs.

The processor 207 is configured through execution of the computation instructions 220 to determine a relative position of the joint at the extent of internal and external rotation during the rotation test. The processor is configured through execution of the computation instructions 220 to determine a relative position of the joint at the extent of Varus and valgus rotation during the VV test. The processor 207 is configured through execution of the computation instructions 220 to determine a relative position of the joint at the extent of anterior and posterior travel during the AP test. The processor 207 is also configured through execution of the computation instructions 220 to determine a zero torque position of the knee for each of the rotation, AP, and VV tests. The processor 207 is configured through execution of the computation instructions 220 to produce load-deformation curves for each of the rotation, AP, and VV tests based on the torque or load data received from the RKT apparatus 54.

The processor 207 is configured through execution of the analysis instructions 222 to determine the equilibrium position for the knee, based on the relative position computations for rotation, AP, and VV motion. The processor 207 is also configured through execution of the analysis instructions 222 to determine the range of motion or extent of motion for the knee, based on the relative position computations for rotation, AP, and VV motion.

Preset data is stored in a database 224. In this example, the memory 206 includes the database 224. Any data store or data structure may be used. For example, the database 224 may be or include a computer-readable storage device or other memory (e.g., a database server) remote from the remainder of the memory 206. The preset data may include stored information pertaining to the rotational and translational motion data recorded for a small or large group of subjects tested in the same manner. The preset data may also include stored leg length measurements and/or other measurements or subject profiles or profile information recorded for a small or large group of subjects tested. The preset date may also include stored torque or load information and/or load-deformation curves for a small or large group of subjects tested. The preset data may be, include, or be based on historical or other data previously acquired for the joint testing. The preset data may include data for both normal and abnormal joints. The preset data may also include stored information pertaining to prior testing done a particular patient for use in comparison to later testing data.

The preset data may include thresholds and/or boundaries. Various types of thresholds may be used. In some cases, one or more thresholds are based on a mean and standard deviation for the joint testing. Alternatively or additionally, the preset data may be or include a distribution and/or a range (e.g., a pair of endpoints). Other types of datasets may be used to analyze the equilibrium position and new extent data. For example, the equilibrium position and motion extent data for a given patient may be compared to equilibrium position and motion extent data for other patients tested, for control patients, from earlier testing of the same patient, or the like. The preset data boundaries may define boundaries differentiating between a normal joint and an abnormal joint, a normal amount of joint play and an abnormal amount of joint play, a normal degree of tibial rotation, VV rotation, and/or AP translation, and the like for comparison to the collected data.

In some cases, the data used by the analysis instructions 222 includes data other than the equilibrium position and motion extent data. For example, the data may include leg length and calf plate position and measurement data, world coordinate system data, local coordinate system data, or the like.

The analysis instructions 222 may cause the processor 207 to incorporate other data into a profile of a joint. For example, the profile may include patient height, weight, and other data indicative of the subject. A computed overall joint play quantity may also be incorporated into the profile. Any data that may be helpful to identifying a joint abnormality may be incorporated. For example, the profile data may specify data indicative of the bones that define the joint under test, such as structural characteristics of the bones, the three-dimensional surfaces of the bones, and the contact points between the bones. Any of these or other parameters may be involved in the analysis (e.g., comparison with the profile data) of the profile of the joint under test implemented via the analysis instructions 222.

In some examples, the processor 207 is configured through execution of the analysis instructions 222 to assess the profile to identify an abnormality of the joint under test. The assessment may include comparing the profile with the profile data to find one or more matches or closest matches. A profile match may identify multiple abnormalities.

The computer 202 and/or the processor 207 and/or the memory 206 and/or the robot 54 may be integrated with one another to any desired extent. In the example of FIG. 11, the RKT apparatus 50 can include another processor 226 and another memory 228. The processor 226 and the memory 228 may be dedicated to supporting the data acquisition and communication functions of the robot 54. For instance, the processor 226 and the memory 228 may not be configured to implement the quantification and evaluation aspects of the system 200. In other cases, the processor 226 and the memory 228 may be involved in the execution of the input instructions 218, the computation instructions 220, and/or the analysis instructions 222. In still other examples, the RKT apparatus 50 and the electronic equipment of the system 200 may share one or more processing and/or memory components.

Each processor 207, 226 may be or include any number or type of processing cores, processors, processing units (e.g., a central processing unit or graphical processing unit), or processing systems. Each processor 207, 226 may be a component in a variety of systems. For example, each processor 207, 226 may be part of a standard personal computer or a workstation. Each processor 207, 226 may be or include one or more general processors, digital signal processors, application specific integrated circuits, field programmable gate arrays, servers, networks, digital circuits, analog circuits, combinations thereof, or other now known or later developed devices for analyzing and processing data.

Each memory 206, 228 may be or include any number or type of computer-readable memories, media, or other devices on which data is stored. Each memory 206, 228 may be or include a main memory, a static memory, or a dynamic memory. Each memory 206, 228 may include, but may not be limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one case, each memory 206, 228 may include a cache or random access memory for a processor. Alternatively or additionally, each memory 206, 228 may be separate from the processor, such as a cache memory of a processor, the system memory, or other memory. Each memory 206, 228 may be or include an external storage device or database for storing data. Examples may include a hard drive, compact disc ("CD"), digital video disc ("DVD"), memory card, memory stick, floppy disc, universal serial bus ("USB") memory device, or any other device operative to store data. Each memory 206, 228 may be operable to store instructions executable by a processor. The functions, acts or tasks illustrated in the figures or described herein may be performed by the programmed processor executing the instructions stored in the memory 206, 228. The functions, acts or tasks may be independent of the particular type of instruction set, storage media, processor or processing strategy and may be performed by software, hardware, integrated circuits, firmware, micro-code and the like, operating alone or in combination. Likewise, processing strategies may include multiprocessing, multitasking, parallel processing and the like.

Figure 22:
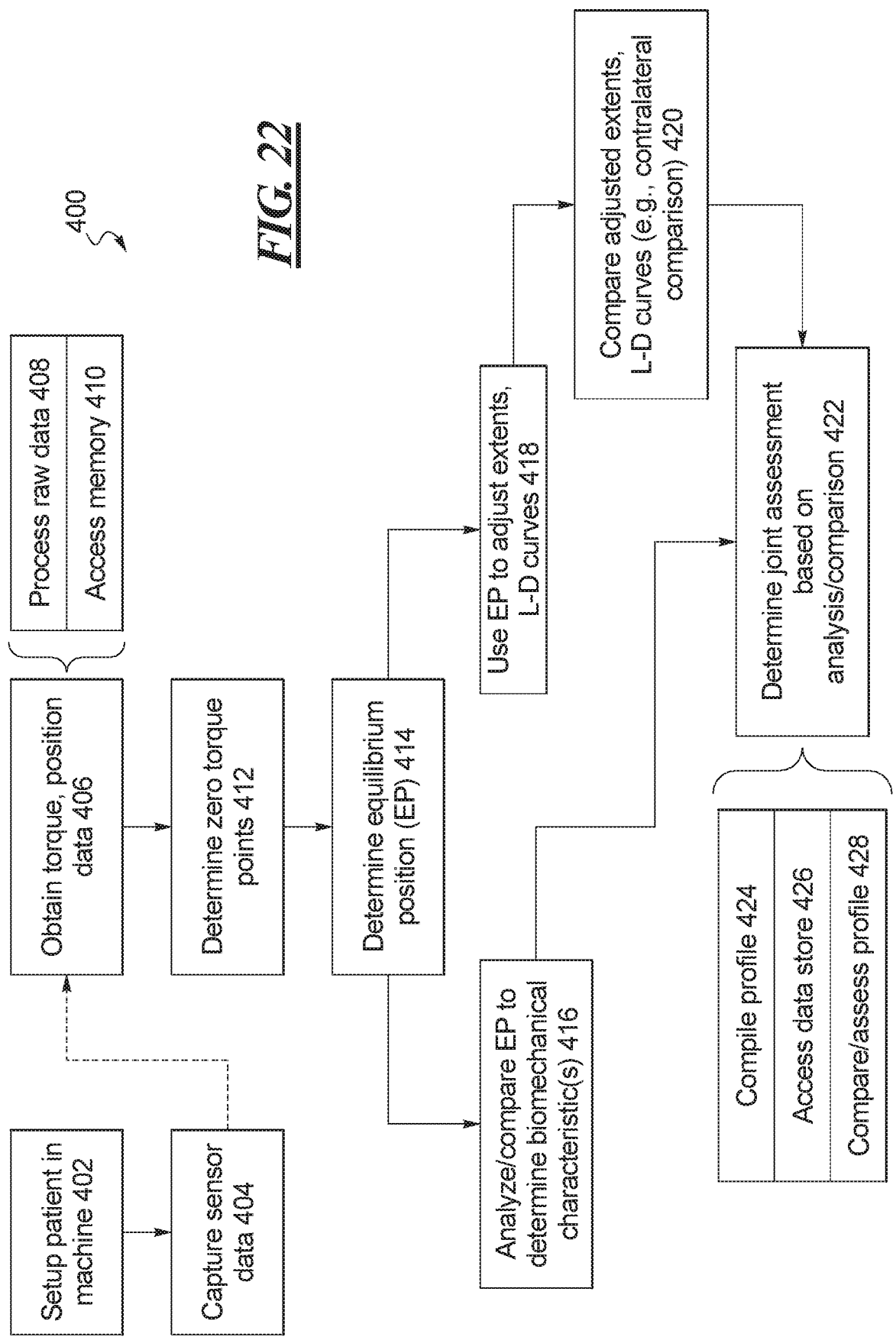
FIG. 22 shows a flow chart of one example of a method to determine and utilize equilibrium position data.

FIG. 22 depicts one example of a method 300 of computing and evaluating joint equilibrium position. The method 300 is computer-implemented. The method 300 may be implemented by the system 200 of FIGS. 10 and/or 11. In some cases, for instance, the processor 207 (FIGS. 10 and 11) implements one or more acts of the method 300. Alternatively or additionally, the processor 226 (FIG. 11) of the RKT apparatus 50 implements one or more acts of the method 300. In these cases, the processor 207 and/or the processor 226 are configured via execution of computer-readable instructions, such as the instructions 218, 220, 222 (FIG. 11) stored in the memory 206 (FIGS. 10 and 11), to cause the processor 212, 226 to implement the method 300. The method 300 may be implemented in additional and/or alternative ways. For instance, one or more acts of the method 300 may be implemented by a remote processor, such as a processor in communication with the processor 212 and/or the processor 226.

A method according to the teachings of the present disclosure is now described with reference to FIG. 22 and using the equilibrium position concept. The method 400 includes an act at block 402 in which the patient is set up in the RKT apparatus 50, as described above. At block 404, the robot 54 is operated to run one or more tests on the patient's knees, During the tests, data is captured from the translation sensors 210 and the rotation or torque sensors or transducers 118, 148, 168.

At block 406, an act includes obtaining torque or load data and position data by the processor 207 and received from the data captured by the sensors at block 404. At block 408, an act includes processing the raw data obtained by the processor 207 according to the computation instructions 220. At block 410, an act includes the processor accessing the memory 206 as needed to obtain relevant stored data and information to be utilized by the processor at block 408.

At block 412, an act includes the processor 207 through the computation instructions 220 calculating the torque zero or neutral position data points for the relevant test(s) or motion(s). At this step, the zero position or neutral position can be determined for tibial rotation, AP tibial translation, and/or VV rotation of the tibia. At block 414, an act includes determining the equilibrium position for the relevant test based on the corresponding neutral position or torque zero condition determined at block 412. The equilibrium position can be computed via or as a function of the rotational data and the translational data, as well as the torque or load data obtained.

Once the equilibrium position is determined at block 414, the equilibrium position can be used for at least two different purposes. For example, at block 416, an act includes analyzing the joint equilibrium position to determine a biomechanical state of the patient's knee. The equilibrium position determined at block 414 can be compared to a data set of healthy and/or injured knees or can be compared to a healthy knee of the patient to assist in making the determination. As another example, at block 418, an act includes using the equilibrium position determined at block 414 to adjust the translation and/or rotation extents relevant to the test(s) and/or to adjust or shift the load-deformation curves to compensate for an altered equilibrium position. At block 420, an act includes again comparing the adjusted extents and/or load-deformation curves contralaterally, i.e., to the data for the patient's other knee, or to a data set of healthy knees or injured knees.

The acts of determining or using at either of blocks 416 or 420 can then be used to assess the state of the patient's knee. The biomechanical characteristics from the acts at block 416 or the adjusted extents or load-deformation curves from the acts at block 420 can be used to assess the patient's knee, indicated at block 422, based in part on the equilibrium position. The assessment at block 422 can be used to compile a profile for the joint under evaluation, as for the act at block 424. The profile may be indicative of the results of comparing the joint data with predetermined or preset data. The profile may include other types of data, such as characteristics of the subject and the computed joint assessment or equilibrium position. A data store, such as the database 224 (FIG. 11) may then be accessed in an act at block 426 to obtain profile data for various joint abnormalities. The profile may then be assessed in an act 428 through, for example, comparing the profile and the abnormality profile data. The assessment at block 422 is for determining the state of the ligaments or structures of the patient's knee. In one example, the joint assessment is to determine whether a knee is considered within a normal range, i.e., whether the joint is normal, not injured, does not warrant surgery or other treatment, or does not warrant further analysis. In another example, the assessment is to determine whether the data exhibits an abnormality of the joint.

The methods described herein may be implemented by software programs executable by a computer system. Further, implementations may include distributed processing, component/object distributed processing, and parallel processing. Alternatively or additionally, virtual computer system processing may be constructed to implement one or more of the methods or functionality as described herein.

The computer-readable media referenced above may be a single medium or multiple media, such as a centralized or distributed database, and/or associated caches and servers that store one or more sets of instructions. The term "computer-readable medium" may also include any tangible medium that may be capable of storing, encoding or carrying a set of instructions for execution by a processor or that may cause a computer system to perform any one or more of the methods or operations disclosed herein. Such computer-readable media may be referred to as "computer-readable storage media."

The computer-readable medium may include a solid-state memory such as a memory card or other package that houses one or more non-volatile read-only memories. The computer-readable medium also may be a random access memory or other volatile re-writable memory. Additionally, the computer-readable medium may include a magneto-optical or optical medium, such as a disk or tapes or other storage device. A digital file attachment to an e-mail or other self-contained information archive or set of archives may be considered a distribution medium that may be a tangible storage medium. Accordingly, the disclosure may be considered to include any one or more of a computer-readable medium or a distribution medium and other equivalents and successor media, in which data or instructions may be stored.

Alternatively or additionally, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system may encompass software, firmware, and hardware implementations.

The preceding description has provided a systematic approach to identifying and addressing error introduced into any system or process meant to identify small changes in motion between the tibia and the femur. It is this ability to identify sources of error, and account for or eliminate such error, that helps in producing an analysis system and methods that can reliably, reproducibly, precisely, and accurately identify biomechanical characteristics in the individual knee that are meaningful for diagnosis. By setting up a world view for reference between knees and a femoral view for reference within the knee, relative and absolute position changes can be identified. By allowing the biomechanics and the anatomy of the knee to define its zero position, examination and clinician error is minimized. The goal is to provide clinicians with biomechanically based tests that will provide accurate, reliable and reproducible predictions of specific knee injuries.

The patient set-up and robot set-up procedures and methods disclosed herein may vary from the examples shown and described. One or more of the specific steps may be performed as described but in a different order. Specific steps may be eliminated or altered and additional steps may be added. The design of the RKT apparatus may vary considerably from the example disclosed herein. As the design of the robot or apparatus varies, so may the steps vary, the order of the steps change, the number of steps change, and/or the specific details of the steps be altered or modified. The specific designs of the knee and thigh stabilizers may change, whether related to how the stabilizers are assembled, constructed, adjusted, locked, released, or the like. Likewise, the specific designs of the axis drives and/or the overall tibia positioning assemblies may also change.

The disclosed set-up procedures have been developed and are being refined in order to aid in reducing error and inconsistency in the test results and the underlying procedures. Some of the disclosed set-up steps are for setting up the patient position relative to the robot. Some of the disclosed set-up steps are for setting up the robot itself. However, all of the steps are conceived to aid in rendering the test procedures and results more accurate and more consistent. According to the disclosure, any patient can be set up relative to the robot in substantially the same way as any other patient. This can make knee laxity data acquired for different patients more directly comparable. According to the disclosure, a given patient can be set up relative to the robot in substantially the same way each time the patient is tested. This can make that patient's test results more relevant when comparing one test to the next. According to the disclosure, the robot can be set up using substantially the same procedure for any patient, other than where patient specific settings are known. This can reduce the amount of error that might otherwise be introduced into any given test.

Many modifications to and other embodiments of the disclosed RKT apparatus, components, methods, uses, and the like set forth herein may come to mind to one skilled in the art to which the invention pertains upon reading this disclosure. Therefore, it is to be understood that the inventions are not to be limited to the specific embodiments and combinations disclosed and that modifications and other embodiments and combinations are intended to be included within the scope of the appended claims. Although specific terms are employed herein, they are used in a generic and descriptive sense only and not for purposes of limitation.

Specific combinations of features, components, aspects, procedures, methods, steps, processes, and arrangements of and for the disclosed RKT apparatus and set-up are disclosed herein. However, one having ordinary skill in the art will understand that each feature, component, aspect, procedure, method, step, process, and arrangement may be used independently or in other combinations not specifically disclosed.

The foregoing description is given for clearness of understanding only, and no unnecessary limitations should be understood therefrom, as modifications within the scope of the invention may be apparent to those having ordinary skill in the art.

Although certain apparatuses, methods, procedures, components, arrangements, and combinations of same for joint analysis and testing have been described herein in accordance with the teachings of the present disclosure, the scope of coverage of this patent is not limited thereto. On the contrary, this patent covers all embodiments of the teachings of the disclosure that fairly fall within the scope of permissible equivalents.

What is claimed is:

1. A knee examination method comprising the steps of:
   situating a patient on a patient support adjacent a robotic knee testing apparatus having a motion tracking system;
   setting up the robotic knee testing apparatus including defining a world coordinate system based on a fixed location of a transmitter of the motion tracking system;
   further setting up the patient including determining one or more local coordinate systems each based on setting up the patient and using a sensor coupled to, and in communication with, the transmitter; and
   operating the robotic knee testing apparatus to manipulate a leg of the patient.

2. A knee examination method according to claim 1, wherein the step of further setting up further includes a step of securing at least a first sensor of the motion tracking system to a first tibia of the leg of the patient whereby the first sensor is used to define a first local coordinate system for the first tibia.

3. A knee examination method according to claim 2, wherein, in the step of securing, the first sensor is a circular sensor.

4. A knee examination method according to claim 2, wherein the step of securing includes the step of further securing a second sensor of the motion tracking system to a second tibia of a second leg of the patient whereby the second sensor is used to define a second local coordinate system for the second tibia.

5. A knee examination method according to claim 1, wherein the step of further setting up includes identifying and recording one or more anatomical points on the leg of the patient using a pointer having the sensor.

6. A knee examination method according to claim 5, wherein the step of identifying and recording includes identifying one or more bony landmarks on the leg of the patient using the pointer, the one or more bony landmarks selected from a tibial tubercle, a midpoint between a medial tibial plateau and a lateral tibial plateau, a medial-lateral midpoint of an anterior proximal tibia and posterior proximal tibia, and a midpoint of a medial malleolus and a lateral malleolus of the leg of the patient.

7. A knee examination method according to claim 5, wherein the step of examining includes calculating a relationship between a coordinate system determined using the one or more bony landmarks and the world coordinate system.

8. A knee examination method according to claim 1, wherein, in the step of setting up, the motion tracking system is an electromagnetic tracking system.

9. A knee examination method according to claim 1, further comprising the step of capturing motion data of the leg and assessing the motion data relative to the world coordinate system.

10. A knee examination method according to claim 1, further comprising the step of capturing motion data of the leg and assessing the motion data relative to the one or more local coordinate systems.

11. A knee examination method according to claim 1, further comprising the step of capturing motion data of the leg and assessing the motion data relative to both the world coordinate system and the one or more local coordinate systems.

12. A knee examination method according to claim 1, further comprising performing each of the steps of setting up the robotic knee testing apparatus, further setting up the patient, and operating the robotic knee testing apparatus for both legs of the patient.

13. A knee examination method according to claim 12, further comprising the step of obtaining data for a world view perspective for both legs of the patient using the world coordinate system and also obtaining data for a local perspective for each leg using the one or more local coordinate systems.

14. A knee examination method according to claim 1, wherein the step of further setting up the patient includes defining a tibial coordinate system of the one or more local coordinate systems for the leg using the motion tracking system whereby a Z axis of the tibial coordinate system extends in a direction of a tibia of the leg.

15. A knee examination method according to claim 14, wherein the step of defining a tibial coordinate system includes defining an origin of the tibial coordinate system as a midpoint between points taken on a medial tibial plateau and a lateral tibial plateau of the leg.

16. A knee examination method according to claim 14, wherein the step of further setting up the patient includes defining a femoral coordinate system of the one or more local coordinate systems for the leg using the motion tracking system whereby the Z axis of the tibial coordinate system is also used as a Z axis of the femoral coordinate system.

17. A knee examination method comprising the steps of:
situating a patient on a patient support adjacent a robotic knee testing apparatus having a motion tracking system;
setting up the robotic knee testing apparatus including defining a world coordinate system based on a fixed location of a transmitter of the motion tracking system;
further setting up the patient including determining one or more local coordinate systems each based on setting up the patient and on one or more robot based points; and
operating the robotic knee testing apparatus to manipulate a leg of the patient,
wherein the step of further setting up includes the step of defining a robot based femoral coordinate system for the leg of the patient including marking one or more fixed points on a knee stabilizer of the robotic knee testing apparatus.

18. A knee examination method according to claim 17, wherein the step of defining a robot based femoral coordinate system includes marking one point at a midpoint of the knee stabilizer above the knee and marking two points laterally spaced apart on the knee stabilizer below the knee.

19. A knee examination method comprising the steps of:
situating a patient on a patient support adjacent a robotic knee testing apparatus having a motion tracking system;
setting up the robotic knee testing apparatus including defining a world coordinate system based on a fixed location of a transmitter of the motion tracking system;
further setting up the patient including determining one or more local coordinate systems each based on setting up the patient and using a sensor in communication with the transmitter; and
operating the robotic knee testing apparatus to manipulate a leg of the patient,
wherein the step of further setting up the patient includes defining a tibial coordinate system of the one or more local coordinate systems for the leg using the motion tracking system whereby a Z axis of the tibial coordinate system extends in a direction of a tibia of the leg,
wherein the step of defining a tibial coordinate system includes defining an origin of the tibial coordinate system as a midpoint between points taken on a medial tibial plateau and a lateral tibial plateau of the leg, and
wherein the step of defining an origin of the tibial coordinate system includes adjusting the origin anteriorly or posteriorly to a midpoint of a thickness of proximal end of the tibia.

20. A knee examination method comprising the steps of:
situating a patient on a patient support adjacent a robotic knee testing apparatus having a motion tracking system;
setting up the robotic knee testing apparatus including defining a world coordinate system based on a fixed location of a transmitter of the motion tracking system;
further setting up the patient including determining one or more local coordinate systems each based on setting up the patient and on one or more robot based points; and
operating the robotic knee testing apparatus to manipulate a leg of the patient,
wherein the step of further setting up the patient includes defining a femoral coordinate system of the leg using the motion tracking system whereby an origin of the femoral coordinate system is central to a triangle defined by taking three points on a portion of the robotic knee testing apparatus surrounding the knee of the leg.

21. A knee examination method according to claim 20, wherein, in the step of defining a femoral coordinate system, the portion of the robotic knee testing apparatus is a knee stabilizer holding the knee of the patient in a substantially fixed position.

22. A knee examination method according to claim 20, wherein the step of defining a femoral coordinate system includes defining a Z axis of a femur of the leg as being parallel to an epicondylar axis of the femur.

23. A knee examination method according to claim 1, further comprising adjusting portions of a drive system of the robotic knee testing apparatus to a zero torque or neutral position relative to each knee of the patient.

\* \* \* \* \*